United States Patent [19] [11] Patent Number: 5,346,920
Sakamoto et al. [45] Date of Patent: Sep. 13, 1994

[54] CARBAMIC ACID DERIVATIVES, AND THEIR PRODUCTION AND USE

[75] Inventors: Noriyasu Sakamoto, Nishinomiya; Hirosi Kisida, Takarazuka; Noritada Matsuo, Itami; Hiroaki Fujimoto; Kimitoshi Umeda, both of Toyonaka, all of Japan

[73] Assignee: Sumitomo Chemical Company, Limited, Osaka, Japan

[21] Appl. No.: 62,328

[22] Filed: May 17, 1993

Related U.S. Application Data

[63] Continuation of Ser. No. 856,734, Mar. 24, 1992, abandoned, which is a continuation-in-part of Ser. No. 705,344, May 24, 1991, abandoned.

[30] Foreign Application Priority Data

Jun. 6, 1990 [JP] Japan ............... 2-149017

[51] Int. Cl.$^5$ ............... C07C 261/00; A01N 37/12
[52] U.S. Cl. ............... 514/539; 560/27
[58] Field of Search ............ 560/27; 514/539; 424/300

[56] References Cited

U.S. PATENT DOCUMENTS

| | | | |
|---|---|---|---|
| 4,215,139 | 7/1980 | Fischer et al. | 520/27 |
| 4,413,010 | 11/1983 | Zurflüh | 560/27 |
| 4,607,051 | 8/1986 | Zurflüh | 560/27 |
| 4,608,389 | 8/1986 | Kisida et al. | 560/27 |
| 5,141,956 | 8/1992 | Karra | 560/27 |

FOREIGN PATENT DOCUMENTS

| | | | |
|---|---|---|---|
| 0004334 | 3/1979 | European Pat. Off. | 560/27 |
| 0390740A | 3/1990 | European Pat. Off. | 560/27 |
| 0390741A | 3/1990 | European Pat. Off. | 560/27 |
| 0394191 | 10/1990 | European Pat. Off. | 560/27 |
| 0395582 | 10/1990 | European Pat. Off. | 560/27 |
| 3832656 | 4/1989 | Fed. Rep. of Germany | 560/27 |
| 0404720 | 12/1990 | Fed. Rep. of Germany | 560/27 |
| 000460472 | 12/1991 | Japan | 560/27 |
| 2084574 | 4/1982 | United Kingdom | 560/27 |

Primary Examiner—José G. Dees
Assistant Examiner—Keith MacMillan
Attorney, Agent, or Firm—Birch, Stewart, Kolasch & Birch

[57] ABSTRACT

A carbamic acid derivative of the formula:

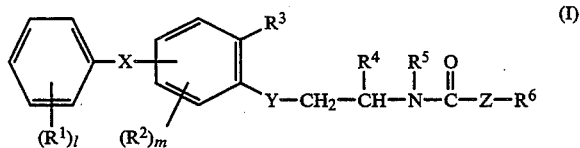

which is useful for the control of insect pests.

17 Claims, No Drawings

CARBAMIC ACID DERIVATIVES, AND THEIR PRODUCTION AND USE

This application is a continuation of application Ser. No. 07/856,734 filed on Mar. 24, 1992, now abandoned which is a continuation-in-part application, of application Ser. No. 07/705,344 filed on May 24, 1991 now abandoned.

BACKGROUND OF THE INVENTION

1. Field of the Invention

The present invention relates to carbamic acid derivatives, and their production and use. More particularly, it relates to novel carbamic acid derivatives, processes for producing them, and methods for controlling insect pests using them.

2. Description of the Prior Art

It is described in U.S. Pat. No. 4,215,139 that certain carbamic acid derivatives are useful as insecticides. However, their insecticidal activity is still not satisfactory.

SUMMARY OF THE INVENTION

As a result of the extensive study seeking compounds showing a satisfactory controlling effect on insects or pests, it has been found that carbamic acid derivatives of the following formula exhibit a sufficiently high juvenile hormone-like activity and can control satisfactorily the growth of insects or pests:

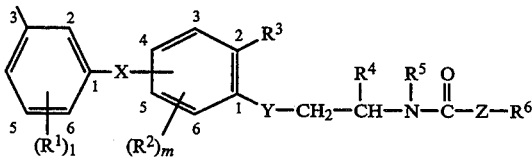
(I)

wherein
$R^1$ is, the same or different, each a hydrogen atom, a halogen atom, a $C_1$-$C_3$ alkyl group, a $C_1$-$C_3$ haloalkyl group, a $C_1$-$C_3$ alkoxy group, a $C_1$-$C_3$ haloalkoxy group, a cyano group or a nitro group;
$R^2$ is, the same or different, each a hydrogen atom, a halogen atom or a methyl group;
$R^3$ is a halogen atom or a methyl group;
$R^4$ is a hydrogen atom or a $C_1$-$C_3$ alkyl group;
$R^5$ is a hydrogen atom, a group of the formula: —S(O)$_n$—N($R^7$)—$R^8$ a group of the formula:

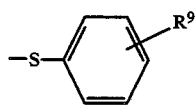

or a group of the formula: —C(O)—C(O)—OR$^{10}$;
$R^6$ is a $C_1$-$C_6$ alkyl group, a $C_1$-$C_6$ haloalkyl group, a $C_3$-$C_6$ alkenyl group, a $C_3$-$C_4$ haloalkenyl group, a $C_3$-$C_6$ alkynyl group, a $C_3$-$C_5$ haloalkynyl group, a $C_3$-$C_6$ alkoxyalkyl group, a $C_3$-$C_6$ alkylthioalkyl group or a $C_3$-$C_6$ cycloalkyl group;
$R^7$ is a $C_1$-$C_6$ alkyl group, an allyl group, a $C_3$-$C_6$ cycloalkyl group or a benzyl group;
$R^8$ is a $C_1$-$C_6$ alkyl group, an allyl group, a $C_3$-$C_6$ cycloalkyl group or a group of the formula: —(CH$_2$)$_p$—C(O)OR$^{11}$;
$R^9$ is a hydrogen atom or a halogen atom;
$R^{10}$ is a $C_1$-$C_{10}$ alkyl group;
$R^{11}$ is a $C_1$-$C_6$ alkyl group;
X is an oxygen atom, a sulfur atom, —NH—, —CO— or —CH$_2$—;
Y and Z are, the same or different, each an oxygen atom or a sulfur atom;
l is an integer of 1 to 5;
m is an integer of 1 to 3;
n is an integer of 0 to 2; and
p is an integer of 0 to 6.

The present invention is based on the above finding.

DETAILED DESCRIPTION OF THE INVENTION

The carbamic acid derivatives of the formula (I) have an excellent juvenile hormone-like activity against various kinds of insect pests. They exhibit actions such as metamorphosis inhibition, embryogenesis inhibition and sterilization and are quite efficacious as growth regulators, chemosterilants, ovicides or reproduction inhibitory agents against various insect pests such as agricultural, forestal, hygienic and stored grain insect pests. Further, they are also efficacious against insect pests having an increased resistance to commercial insecticides or pesticides.

In the formula (I) showing the carbamic acid derivatives of the invention, the symbols have the meanings as defined above. Examples of "$C_1$-$C_3$ alkyl" are methyl, ethyl, n-propyl and isopropyl. Examples of "$C_1$-$C_3$ haloalkyl" include trifluoromethyl, difluoromethyl, 2-fluoroethyl, 1-fluoroethyl, 1,2-difluoroethyl, 2,2,2-trifluoroethyl, 2-chloroethyl, 3-fluoro-n-propyl, 2-fluoro-n-propyl, 1-fluoro-n-propyl, 3-chloro-n-propyl and 3-bromo-n-propyl. Examples of "$C_1$-$C_3$ alkoxy" include methoxy, ethoxy, n-propoxy and isopropoxy. Examples of "$C_1$-$C_3$ haloalkoxy" are trifluoromethoxy, difluoromethoxy, bromodifluoromethoxy, 2-fluoroethoxy, 2,2,2-trifluoroethoxy, 1-chloroethoxy, 1,1,2-trifluoroethoxy, 3-fluoro-n-propoxy, 2-chloro-1,1,2-trifluoroethoxy, 2-fluoro-n-propoxy, 2-chloroethoxy, 3-chloro-n-propoxy, 3-bromo-n-propoxy and 1,1,2,2-tetrafluoroethoxy.

Examples of "$C_1$-$C_6$ alkyl" are methyl, ethyl, n-propyl, isopropyl, n-butyl, sec-butyl, isobutyl, tertbutyl, n-pentyl, neo-pentyl, 2-methyl-n-butyl, 1-methyl-n-butyl, 1-ethyl-n-propyl, 1,1-dimethyl-n-propyl, n-hexyl, 1-methyl-n-pentyl, 2-methyl-n-pentyl, 3-methyl-n-pentyl, 4-methyl-n-pentyl, 3,3-dimethyl-n-butyl, 2,2-dimethyl-n-butyl, 1,1-dimethyl-n-butyl, 2-ethyl-n-butyl, 1-ethyl-n-butyl and 1,3-dimethyl-n-butyl. Examples of "$C_1$-$C_6$ haloalkyl" include difluoromethyl, trifluoromethyl, 2-fluoroethyl, 2-chloroethyl, 2-bromoethyl, 2-iodoethyl, 2,2,2-trifluoroethyl, 2,2,2-trichloroethyl, 2,2,2-tribromoethyl, 3-fluoro-n-propyl, 2,2,3,3,3-pentafluoro-n-propyl, 2-chloro-1-methyl-n-propyl, 3-chloro-n-propyl, 2-chloro-n-propyl, 2,3-dichloro-n-propyl, 1,3-dichloro-2-n-propyl, 3-bromo-n-propyl, 2-bromo-n-propyl, 1-bromo-2-n-propyl, 2,3-dibromo-n-propy!, 3-iodo-n-propyl, 4-fluoro-n-butyl, 4,4,4-trifluoro-n-butyl, 3,3,4,4,4-pentafluoro-2-n-butyl, 2,2,3,3,4,4,4-heptafluoro-n-butyl, 4-chloro-n-butyl, 3-chloro-n-butyl, 2,3,4-trichloro-n-butyl, 4-bromo-n-butyl, 3-bromo-n-butyl, 4-iodo-n-butyl, 5-fluoro-n-pentyl, 5-chloro-n-pentyl, 5-bromo-n-pentyl, 6-fluoro-n-hexyl, 6-chloro-n-hexyl and 6-bromo-n-hexyl. Examples of "$C_3$-$C_6$ alkenyl" are allyl, 2-methylallyl, 1,1-dimethyl-2-n-propenyl, 2-n-butenyl, 3-n-butenyl, 3-methyl-2-n-butenyl, 2-methyl-2-n-butenyl, 2-methyl-3-n-butenyl, 2-n-pentenyl, 2-n-hexenyl and 5-n-hexenyl. Examples of "C$_3$–C$_4$ haloalkenyl" include 2,3-dichloroallyl, 2,3-dibromoallyl, 2-chloro-2-n-propenyl, 3-chloro-2-n-propenyl, 2-bromo-2-n-propenyl, 2-chloromethyl-2-n-propenyl, 2-chloro-3-n-butenyl, 3-chloro-2-n-butenyl, 4-chloro-2-n-butenyl and 4-bromo-2-n-butenyl. Examples of "C$_3$–C$_6$ alkynyl" include 1-n-propynyl, 1-methyl-2-n-propynyl, 1-ethyl-2-n-propynyl, 1-ethynyl-n-butyl, 2-n-butynyl, 1-ethyl-2-n-butynyl, 1-n-propynyl-2-n-butynyl, 2-n-pentynyl, 4-methyl-2-n-pentynyl, 1-methyl-2-n-pentynyl, 2-n-hexynyl and 3-n-hexynyl. Examples of "C$_3$–C$_5$ haloalkynyl" are 3-chloro-2-propynyl, 3-chloro-n-propynyl, 3-bromo-n-propynyl, 1-chloro-2-n-butynyl, 4-chloro-3-n-butynyl, 1-bromo-2-n-butynyl, 4-bromo-3-n-butynyl, 5-chloro-4-n-pentynyl, 5-bromo-4-n-pentynyl, 1-bromo-2-n-pentynyl and 1-bromo-4-n-pentynyl. Examples of "C$_3$–C$_6$ alkoxyalkyl" include 2-methoxyethyl, 2-ethoxyethyl, 2-isopropoxyethyl, 3-methoxy-n-propyl, 2-methoxy-n-propyl, 2-ethoxy-n-propyl, 3-(n-propoxy)-n-propyl, 4-methoxy-n-butyl and 4-ethoxy-n-butyl. Examples of "C$_3$–C$_6$ alkylthioalkyl" include 2-methylthioethyl, 2-ethylthioethyl, 3-methylthio-n-propyl, 2-methylthio-n-propyl, 2-ethylthio-n-propyl, 3-(n-propyl)thio-n-propyl, 4-methylthio-n-butyl and 4-ethylthio-n-butyl. Examples of "C$_3$–C$_6$ cycloalkyl" are cyclopropyl, cyclobutyl, cyclopentyl and cyclohexyl.

Examples of "C$_1$–C$_{10}$ alkyl" include methyl, ethyl, n-propyl, isopropyl, n-butyl, sec-butyl, isobutyl, tertbutyl, n-pentyl, n-hexyl, n-heptyl, n-octyl, n-nonyl and n-decyl. Examples of the halogen atom are chlorine, bromine, fluorine, iodine, etc.

Among the carbamic acid derivatives (I), preferred are those wherein R$^1$ is, the same or different, a hydrogen atom, a fluorine atom, a chlorine atom or a methyl group; R$^2$ is a hydrogen atom or a chlorine atom; R$^3$ is a halogen atom; R$^4$ and R$^5$ are each a hydrogen atom; R$^6$ is a C$_1$–C$_5$ alkyl group, a C$_2$ haloalkyl group, an allyl group, a propargyl group or a methoxyethyl group; X is an oxygen atom or a methylene group; Y is an oxygen atom; Z is an oxygen atom or a sulfur atom; l is an integer of 1 or 2; m is an integer of 1; a group of the formula:

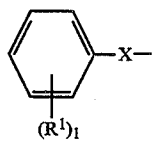

(hereinafter referred to as "optionally substituted phenyl-X- group") is present at the 4- or 5-position on the benzene ring.

More preferred are those wherein R$^1$ is a fluorine atom or a chlorine atom; R$^2$ is a hydrogen atom or a chlorine atom at the 5-position; R$^3$ is a chlorine atom; R$^4$ and R$^5$ are each a hydrogen atom; R$^6$ is a methyl group, an ethyl group or a 2-chloroethyl group; X is an oxygen atom or a methylene group; Y and Z are each an oxygen atom; l is an integer of 2; m is an integer of 1; and the optionally substituted phenyl-X- group is present at the 4-position. The optionally substituted phenyl group in said optionally substituted phenyl-X- group may represent 3,5-difluorophenyl or 3,4-dichlorophenyl. Also, the optionally substituted phenyl group may represent 3-chlorophenyl, 4-chlorophenyl or 4-fluorophenyl when X is an oxygen atom, or phenyl when X is a methylene group.

Most preferred are those wherein R$^1$ is a fluorine atom; R$^2$ is a hydrogen atom or a chlorine atom at the 5-position; R$^3$ is a chlorine atom; R$^4$ and R$^5$ are each a hydrogen atom; R$^6$ is a methyl group or an ethyl group; X is an oxygen atom or a methylene group; Y and Z are each an oxygen atom; l is an integer of 2; m is an integer of 1; and the optionally substituted phenyl-X- group is present at the 4-position. The optionally substituted phenyl group in said optionally substituted phenyl-X- group may represent 3,5-difluorophenyl. Also, the optionally substituted phenyl group may represent 3,4-dichlorophenyl or 3-chlorophenyl when X is an oxygen atom, or phenyl when X is a methylene group.

The carbamic acid derivatives (I) can be produced by various processes, of which some typical examples will be hereinafter explained in details.

PROCESS A

Production of the carbamic acid derivatives (I) wherein R$^5$ is a hydrogen atom:

The carbamic acid derivative (I) wherein R$^5$ is a hydrogen atom, which is representable by the formula:

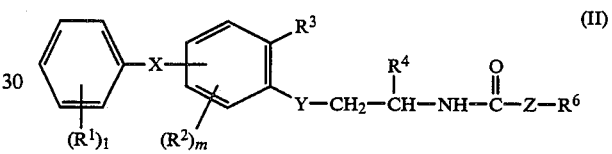

wherein R$^1$, R$^2$, R$^3$, R$^4$, R$^6$, X, Y, Z, l and m are each as defined above can be produced by reacting an amine compound of the formula:

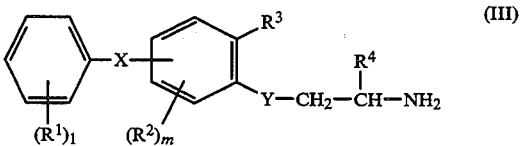

wherein R$^1$, R$^2$, R$^3$, R$^4$, X, Y, l and m are each as defined above with an acid halide of the formula:

wherein R$^6$ and Z are each defined above and L$^1$ is a halogen atom.

The reaction is usually carried out in an inert solvent in the presence of a base at a temperature of from about $-20°$ C. to the boiling point of the inert solvent, preferably from about $-5°$ C. to the boiling point of the inert solvent. When desired, an ammonium salt (e.g. triethyl benzyl ammonium chloride) may be added to the reaction system as a catalyst.

The molar proportion of the amine compound (III) and the acid halide (IV) to be used in the reaction may be from about 1 : 3 to 3 : 1, preferably around 1 : 1. Examples of the base are alkali metal carbonates (e.g. potassium carbonate), organic bases (e.g. triethylamine, pyridine), etc. Examples of the inert solvent are ketones (e.g. acetone, methyl ethylketone), hydrocarbons (e.g. hexane, benzene, toluene), ethers (e.g. diethyl ether, diisopropyl ether, tetrahydrofuran, dioxane), halogenated hydrocarbons (e.g. dichloromethane, chloroform, 1,2-dichloroethane, chlorobenzene), nitriles (e.g. acetonitrile), nitro compounds (e.g. nitromethane), dimethyl sulfoxide, water or mixtures thereof.

After completion of the reaction, post-treatment follows in a per se conventional manner such as extraction with an organic solvent and concentration. When desired, the product may further be purified by chromatography, distillation, recrystallization or the like.

PROCESS B

Production of the carbamic acid derivatives (I) wherein $R^5$ is a hydrogen atom:

The carbamic acid derivative (II) can be produced by reacting an isocyanate compound of the formula:

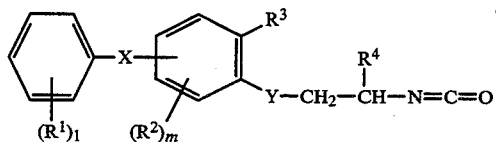
(V)

wherein $R^1$, $R^2$, $R^3$, $R^4$, X, Y, l and m are each as defined above with a (thio)alcohol of the formula:

$$R^6—Z—H \quad (VI)$$

wherein $R^6$ and Z are each as defined above.

The reaction is usually carried out in an inert solvent in the presence of a catalyst at a temperature of from about −20° C. to the boiling solvent of the inert solvent, preferably from about −5° C. to the boiling point of the inert solvent.

The molar proportion of the isocyanate compound (V) and the (thio)alcohol (VI) to be used in the reaction may be from about 1 : 3 to 3 : 1, preferably around 1 : 1. Examples of the catalyst are an organic base (e.g. triethylamine, pyridine, sodium acetate), an acid (e.g. aluminium chloride, hydrogen chloride, boron trifluoride ether complex ($BF_3.(C_2H_5)_2O$)), etc. Examples of the inert solvent are hydrocarbons (e.g. benzene, toluene, hexane, etc.; ether such as diethyl ether, diisopropyl ether, tetrahydrofuran, dioxane, etc.; polar solvent such as N,N-dimethylformamide, dimethylsulfoxide, hexamethylphosphoric triamide, etc.; halogenated hydrocarbons such as dichloromethane, chloroform, 1,2-dichloroethane, chlorobenzene, etc.; nitriles such as acetonitrile etc.; nitro compounds such as nitromethane etc., or mixtures thereof.

After completion of the reaction, post-treatment follows in a per se conventional manner such as extraction with an organic solvent and concentration. When desired, the product may further be purified by chromatography, distillation, recrystallization or the like.

PROCESS C

Production of the carbamic acid derivatives (I) wherein $R^5$ is a hydrogen atom:

The carbamic acid derivative (II) can be produced by reacting a (thio)phenol compound of the formula:

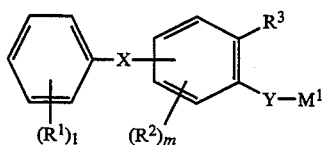
(VII)

wherein $R^1$, $R^2$, $R^3$, X, Y, l and m are each as defined above and $M^1$ is an alkali metal atom or a hydrogen atom with a reactive alkane of the formula:

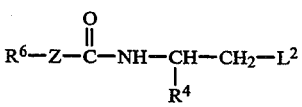
(VIII)

wherein $R^4$, $R^6$ and Z are each as defined above and $L^2$ is a halogen atom, a methanesulfonyloxy group or a toluenesulfonyloxy group.

The reaction is normally carried out in an inert solvent in the presence of a base at a temperature of from about −20° C. to the boiling point of the inert solvent, preferably from about −5° C. to the boiling point of the inert solvent. When $M^1$ in the (thio)phenol compound (VII) is an alkali metal atom, it is not necessarily required to use the base.

The molar proportion of the (thio)phenol compound (VII) and the reactive alkane (VIII) to be used in the reaction may be from about 1 : 3 to 3 : 1, preferably around 1 : 1. Examples of the inert solvent are lower alcohols (e.g. methanol, ethanol, propanol, isopropanol, tertbutanol), ketones (e.g. acetone, methyl ethyl ketone), hydrocarbons (e.g. hexane, benzene, toluene), ethers (e.g. diethyl ether, diisopropyl ether, tetrahydrofuran, dioxane), polar solvents (e.g. N,N-dimethylformamide, dimethylsufoxide, hexamethyl phosphoric triamide), halogenated hydrocarbons (e.g. dichloromethane, chloroform, 1,2-dichloroethane, chlorobenzene), nitriles (e.g. acetonitrile), nitro compounds (e.g. nitromethane), water or mixtures thereof. Examples of the base are alkali metal hydroxides (e.g. sodium hydroxide, potassium hydroxide), alkali metal carbonates (e.g. potassium carbonate), alkali metals (e.g. metallic sodium), alkali metal hydrides (e.g. sodium hydride), organic bases (e.g. sodium methoxide, sodium ethoxide, triethylamine, pyridine), etc. When desired, ammonium salts such as triethyl benzylammonium chloride may be added to the reaction system as a catalyst.

After completion of the reaction, post-treatment follows in a per se conventional manner such as extraction with an organic solvent and concentration. When desired, the product may further be purified by chromatography, distillation, recrystallization or the like.

PROCESS D

Production of the carbamic acid derivative (I) wherein $R^5$ is a hydrogen atom and Z is a sulfur atom:

The carbamic acid derivative (I) wherein $R^5$ is a hydrogen atom and Z is a sulfur atom, which is representable by the formula:

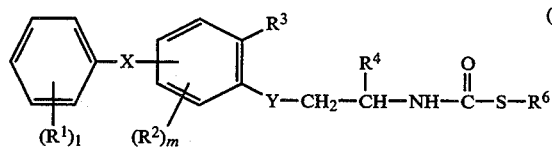 (IX)

wherein $R^1$, $R^2$, $R^3$, $R^4$, $R^6$, X, Y, l and m are each as defined above, can be produced by reacting a thiocarbamic acid compound of the formula:

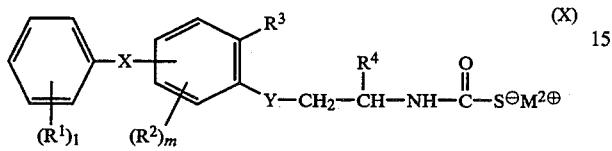 (X)

wherein $R^1$, $R^2$, $R^3$, $R^4$, X, Y, l and m are each as defined above and $M^{2\oplus}$ is an alkali metal ion or a quaternary ammonium ion with a reactive alkane of the formula:

$$R^6—L^3 \quad (XI)$$

wherein $R^6$ is the same as defined above and $L^3$ is a halogen atom, a methanesulfonyloxy group or a toluenesulfonyloxy group.

The reaction is normally effected in an inert solvent at a temperature of from about −20° C. to the boiling point of the inert solvent, preferably from −5° C. to the boiling point of the inert solvent.

The proportion of the thiocarbamic acid compound (X) and the reactive alkane (XI) to be used for the reaction may be optional, but it is normally preferred to be in a nearly equal molar ratio. Examples of the inert solvent which are lower alcohols (e.g. methanol, ethanol. propanol, isopropanol, tert-butanol), ketones (e.g. acetone, methyl ethyl ketone), hydrocarbons (e.g. hexane, benzene, toluene), ethers (e.g. diethyl ether, diisopropyl ether, tetrahydrofuran, dioxane), polar solvents (e.g. N,N-dimethylformamide, dimethylsufoxide, hexamethylphosphoric triamide), halogenated hydrocarbons (e.g. dichloromethane, chloroform, 1,2-dichloroethane, chlorobenzene), nitriles (e.g. acetonitrile), nitro compounds (e.g. nitromethane), water or mixtures thereof. When desired, ammonium salts such as triethylbenzylammonium chloride may be added to the reaction mixture as a catalyst.

After completion of the reaction, post-treatment follows in a per se conventional manner such as extraction with an organic solvent and concentration. When desired, the product may further be purified by chromatography, distillation, recystallization or the like.

PROCESS E

Production of the carbamic acid derivative (I) wherein $R^5$ is not a hydrogen atom:

The carbamic acid derivative (I) wherein $R^5$ is not a hydrogen atom, which is representable by the formula:

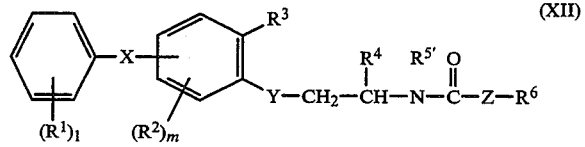 (XII)

wherein $R^1$, $R^2$, $R^3$, $R^4$, $R^6$, X, Y, Z, l and m are each as defined above and $R^{5'}$ is a group of the formula: —S(O)$_n$—N($R^7$)—$R^8$, a group of the formula:

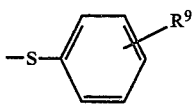

or a group of the formula: —C(O)—C(O)—OR$^{10}$, can be produced by reacting a carbamic acid compound of the formula:

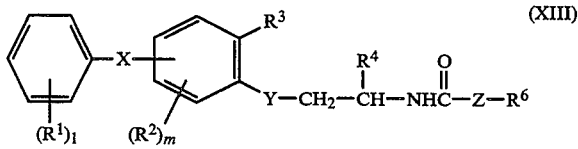 (XIII)

wherein $R^1$, $R^2$, $R^3$, $R^4$, $R^6$, X, Y, Z, l and m are each as defined above with a reactive alkane of the formula:

$$R^{5'}—L^4 \quad (XIV)$$

wherein $R^{5'}$ is the same as defined above and $L^4$ is a halogen atom.

The reaction is ordinarily performed in an inert solvent in the presence of a base at a temperature of from about −10° C. to the boiling point of the inert solvent.

The proportion of the reagents, i.e. the carbamic acid compound (XIII), the reactive alkane (XIV) and the base, to be used for the reaction may be optional. In usual, however, the amounts of the reactive alkane (XIV) and the base may be respectively from about 1 to 2 moles and from about 0.9 to 20 moles to one mole of the carbamic acid compound (XIII). Examples of the inert solvent are ketones (e.g. acetone, methyl ethyl ketone), hydrocarbons (e.g. hexane, benzene, toluene), ethers (e.g. diethyl ether, diisopropyl ether, tetrahydrofuran, dioxane), halogenated hydrocarbons (e.g. dichloromethane, chloroform, 1,2-dichloroethane, chlorobenzene), nitriles (e.g. acetonitrile), nitro compounds (e.g. nitromethane), pyridine or mixtures thereof. Examples of the base are alkali metal carbonates (e.g. potassium carbonate), alkali metal hydrides (e.g. sodium hydride), organic bases (e.g. sodium methoxide, sodium ethoxide, triethylamine, pyridine), etc.

After completion of the reaction, post-treatment follows in a per se conventional manner such as extraction with an organic solvent and concentration. If necessary, the product may further be purified by chromatography, distillation, recystallization or the like.

The carbamic acid derivatives (I) of the invention thus produced have optical isomers due to some asymmetric carbon atoms therein and are usually obtained in a mixture of those optical isomers. Such mixture may be separated into each optical isomer by application of an appropriate separation procedure thereto. These optical isomers and their mixtures at any mixing ration fall within the scope of the invention.

Some of the starting compounds in the above processes, i.e. the acid halide (IV), the (thio)alcohol (VI), the reactive alkane (VIII), the reactive alkane (XI) and the reactive alkane (XIV), are avilable on the commercial market or can be readily produced from appropriate commercial products by a conventional procedure, for instance, as described in J. Prakt. Chem., 21, 124 (1880). Other starting compounds, i.e. the amine compound (III), the isocyanate compound (V), the (thio)- phenol compound (VII) and the thiocarbamic acid compound (X) may be prepared, for instance, by the chemical conversions as shown in Reaction Schemes 1 and 2.

Reaction Scheme 1

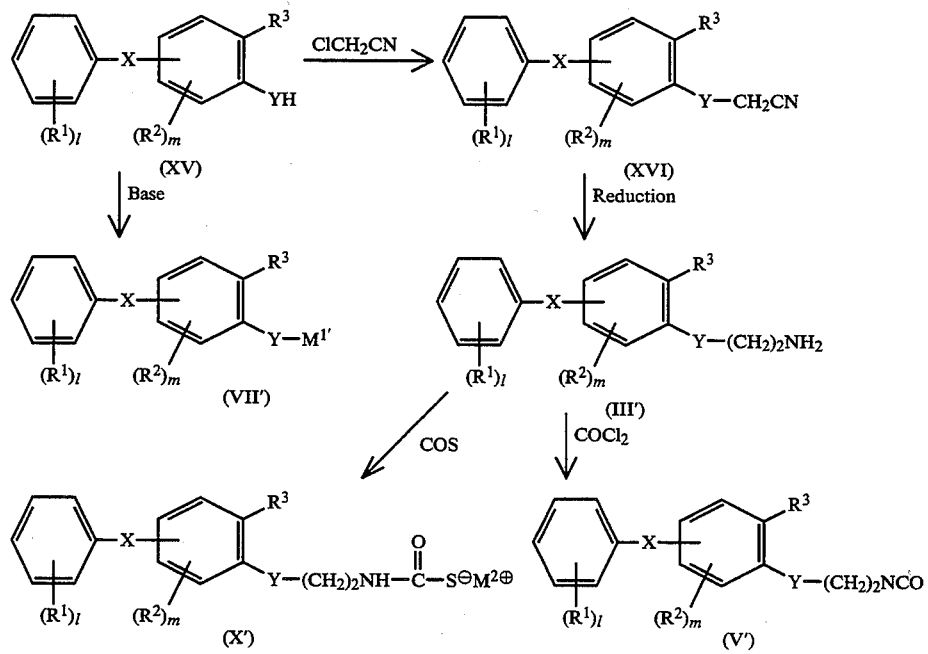

wherein $R^1$, $R^2$, $R^3$, $R^4$, X, Y, l, m and $M^2$ are each as defined above and $M^{1'}$ is an alkali metal atom.

Reaction Scheme 2

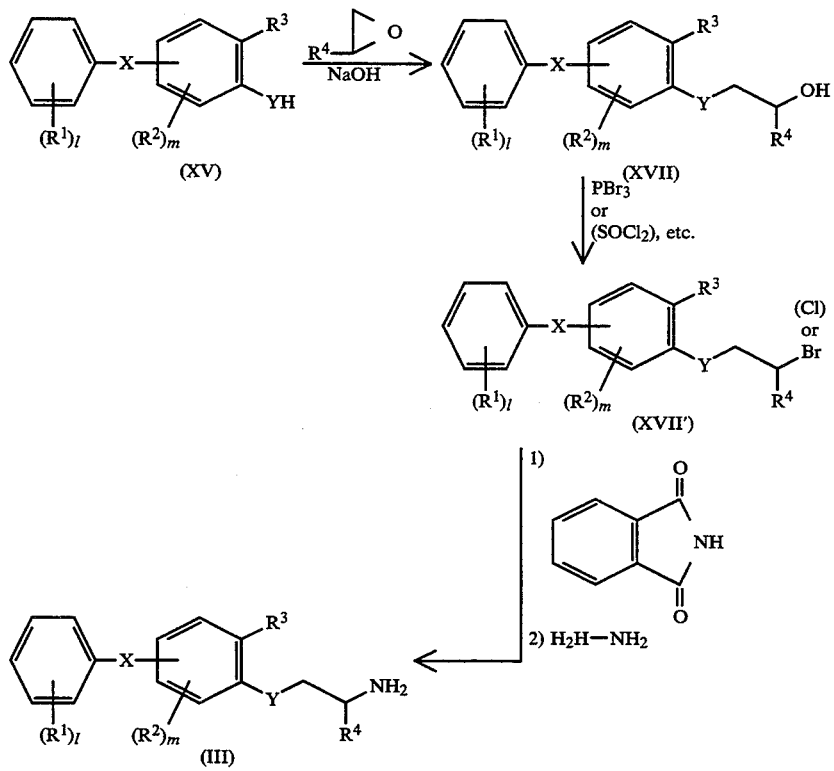

wherein $R^1$, $R^2$, $R^3$, $R^4$, X, Y, l and m are each as defined above.

The (thio) phenol compound (VII) wherein $M^1$ is a hydrogen atom may be also produced according to the chemical conversions as shown in Reaction scheme 3.

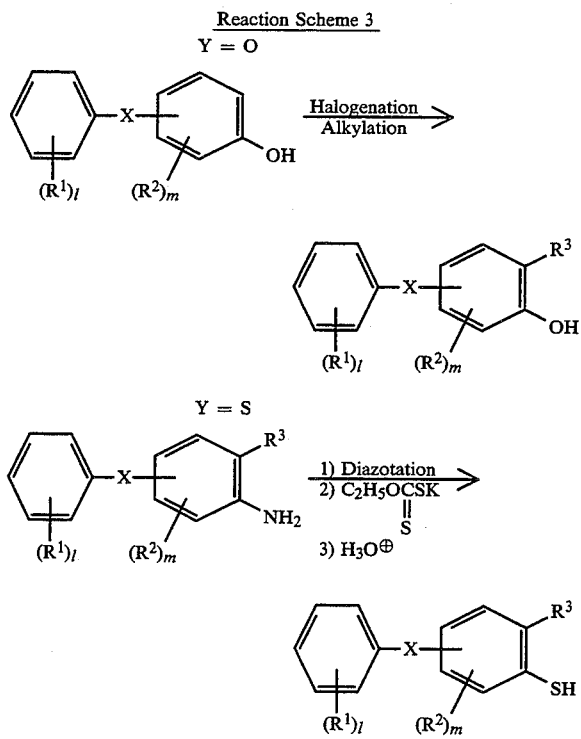

wherein $R^1$, $R^2$, $R^3$, X, l and m are each as defined above.

In the above chemical conversions, each reaction may be carried out by a per se conventional procedure. For instance, the (thio)phenol compound (VII) wherein $R^3$ is a chlorine atom, Y is an oxygen atom and $M^1$ is a hydrogen atom is produced by reacting the corresponding non-chlorinated compound with a chlorinating agent, optionally in an inert solvent.

The molar proportion of the starting non-chlorinated compound and the chlorinating agent to be used for the reaction is not limitative, but usually the chlorinating agent is used in nearly an equvalent molar amount or somewhat an excessive amount. Examples of the chlorinating agent are chlorine, tert-butylhypochlorous acid, sulfuryl chloride, etc. Examples of the inert solvent are dichloromethane, dichloroethane, carbon tetrachloride, benzene, acetic acid, etc. The chlorinating agent is itself available as a reaction medium when it is in liquid. The reaction temperature is usually from about $-80°$ C. to the refluxing temperature of the reaction system, preferably from about $-20°$ C. to the refluxing temperature of the reaction system.

After completion of the reaction, post-treatment may follow in a per se conventional manner such as extraction with an organic solvent and concentration. When necessary or desired, the product may further be purified by chromatography, distillation, recrystallization, etc.

Other halogenation such as fluorination or bromination and alkylation such as methylation may be carried out by a per se conventional procedure as disclosed in Tetrahedron Lett., 27, 4465 (1986), J. Org. Chem., 32, 2358 (1967), Tetrahedron Lett., 899 (1974), etc.

Said non-chlorinated compound used as the starting material in the above reaction may be produced by various procedures, of which some examples are shown in Reaction Scheme 4.

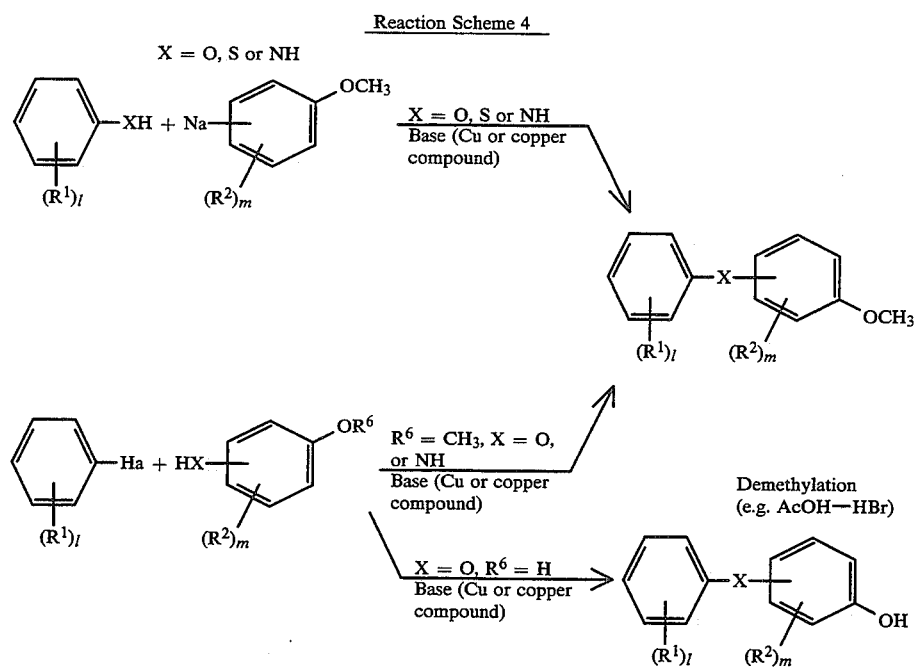

-continued
Reaction Scheme 4
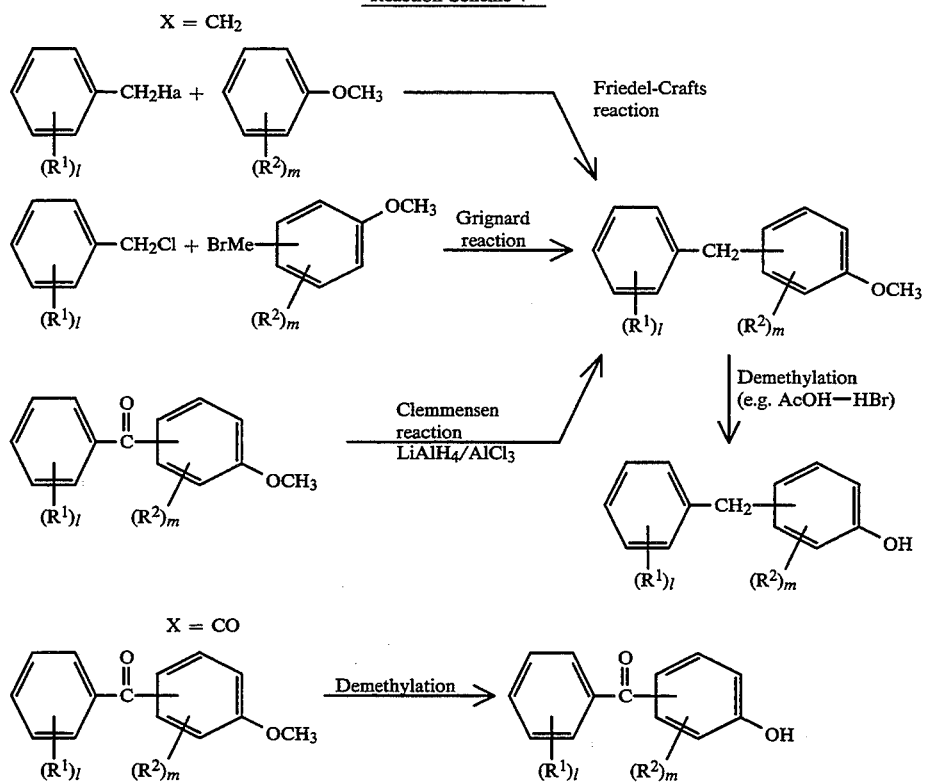
wherein Ha is a halogen atom and $R^1$, $R^2$, l and m are each as defined above.
Typical examples of the carbamic acid derivatives (I) according to the invention are shown in Tables 1 to 6.

TABLE 1

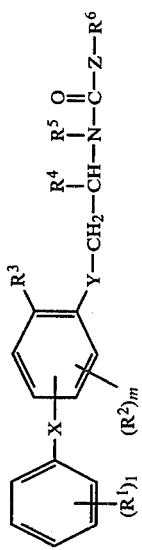

(I) R⁵ is a hydrogen atom and A is present at the 4-position.

| (R¹)l | X | (R²)m | R³ | Y | R⁴ | Z | R⁶ |
|---|---|---|---|---|---|---|---|
| H | O | H | Cl | O | H | O | C₂H₅ |
| H | O | H | F | O | H | O | C₂H₅ |
| H | O | H | Br | O | H | O | C₂H₅ |
| H | O | H | CH₃ | O | H | O | C₂H₅ |
| 3-F | O | H | Cl | O | H | O | C₂H₅ |
| 3-F | O | H | F | O | H | O | C₂H₅ |
| 3-F | O | H | Br | O | H | O | C₂H₅ |
| 3-F | O | H | CH₃ | O | H | O | C₂H₅ |
| 2-F | O | H | Cl | O | H | O | C₂H₅ |
| 2-F | O | H | F | O | H | O | C₂H₅ |
| 2-F | O | H | Br | O | H | O | C₂H₅ |
| 2-F | O | H | CH₃ | O | H | O | C₂H₅ |
| 4-F | O | H | Cl | O | H | O | C₂H₅ |
| 4-F | O | H | F | O | H | O | C₂H₅ |
| 4-F | O | H | Br | O | H | O | C₂H₅ |
| 4-F | O | H | CH₃ | O | H | O | C₂H₅ |
| 2-Cl | O | H | Cl | O | H | O | C₂H₅ |
| 2-Cl | O | H | F | O | H | O | C₂H₅ |
| 2-Cl | O | H | Br | O | H | O | C₂H₅ |
| 2-Cl | O | H | CH₃ | O | H | O | C₂H₅ |
| 3-Cl | O | H | Cl | O | H | O | C₂H₅ |
| 3-Cl | O | H | F | O | H | O | C₂H₅ |
| 3-Cl | O | H | Br | O | H | O | C₂H₅ |
| 3-Cl | O | H | CH₃ | O | H | O | C₂H₅ |
| 4-Cl | O | H | Cl | O | H | O | C₂H₅ |
| 4-Cl | O | H | F | O | H | O | C₂H₅ |
| 4-Cl | O | H | Br | O | H | O | C₂H₅ |
| 4-Cl | O | H | CH₃ | O | H | O | C₂H₅ |
| 2-Br | O | H | Cl | O | H | O | C₂H₅ |
| 2-Br | O | H | F | O | H | O | C₂H₅ |
| 2-Br | O | H | Br | O | H | O | C₂H₅ |
| 2-Br | O | H | CH₃ | O | H | O | C₂H₅ |
| 3-Br | O | H | Cl | O | H | O | C₂H₅ |
| 3-Br | O | H | F | O | H | O | C₂H₅ |
| 3-Br | O | H | Br | O | H | O | C₂H₅ |
| 3-Br | O | H | CH₃ | O | H | O | C₂H₅ |
| 4-Br | O | H | Cl | O | H | O | C₂H₅ |
| 4-Br | O | H | F | O | H | O | C₂H₅ |
| 4-Br | O | H | Br | O | H | O | C₂H₅ |
| 4-Br | O | H | CH₃ | O | H | O | C₂H₅ |
| 3-I | O | H | Cl | O | H | O | C₂H₅ |
| 3-I | O | H | F | O | H | O | C₂H₅ |

-continued

| | | | | | | | |
|---|---|---|---|---|---|---|---|
| 3-I | O | H | Br | O | H | O | C₂H₅ |
| 3-I | O | H | CH₃ | O | H | O | C₂H₅ |
| 4-I | O | H | Cl | O | H | O | C₂H₅ |
| 4-I | O | H | F | O | H | O | C₂H₅ |
| 4-I | O | H | Br | O | H | O | C₂H₅ |
| 4-I | O | H | CH₃ | O | H | O | C₂H₅ |
| 3-CH₃ | O | H | Cl | O | H | O | C₂H₅ |
| 3-CH₃ | O | H | Br | O | H | O | C₂H₅ |
| 3-CH₃ | O | H | F | O | H | O | C₂H₅ |
| 3-CH₃ | O | H | CH₃ | O | H | O | C₂H₅ |
| 4-CH₃ | O | H | Cl | O | H | O | C₂H₅ |
| 4-CH₃ | O | H | Br | O | H | O | C₂H₅ |
| 4-CH₃ | O | H | F | O | H | O | C₂H₅ |
| 4-CH₃ | O | H | CH₃ | O | H | O | C₂H₅ |
| 3-CF₃ | O | H | Cl | O | H | O | C₂H₅ |
| 3-CF₃ | O | H | Br | O | H | O | C₂H₅ |
| 3-CF₃ | O | H | F | O | H | O | C₂H₅ |
| 3-CF₃ | O | H | CH₃ | O | H | O | C₂H₅ |
| 4-CF₃ | O | H | Cl | O | H | O | C₂H₅ |
| 4-CF₃ | O | H | Br | O | H | O | C₂H₅ |
| 4-CF₃ | O | H | F | O | H | O | C₂H₅ |
| 4-CF₃ | O | H | CH₃ | O | H | O | C₂H₅ |
| 3-C₂H₅ | O | H | Cl | O | H | O | C₂H₅ |
| 2-CF₃ | O | H | Cl | O | H | O | C₂H₅ |
| 3-OCH₃ | O | H | Cl | O | H | O | C₂H₅ |
| 4-OCHF₂ | O | H | Cl | O | H | O | C₂H₅ |
| 4-C₂H₅ | O | H | Cl | O | H | O | C₂H₅ |
| 3-CN | O | H | Cl | O | H | O | C₂H₅ |
| 4-iso-C₃H₇ | O | H | Cl | O | H | O | C₂H₅ |
| 4-OCH₃ | O | H | Cl | O | H | O | C₂H₅ |
| 3-NO₂ | O | H | Cl | O | H | O | C₂H₅ |
| 4-CN | O | H | Cl | O | H | O | C₂H₅ |
| 4-NO₂ | O | H | Cl | O | H | O | C₂H₅ |
| H | O | H | Cl | S | H | O | C₂H₅ |
| H | O | H | Cl | CH₂ | H | O | C₂H₅ |
| H | O | H | Cl | NH | H | O | C₂H₅ |
| H | O | H | Cl | O | H | S | C₂H₅ |
| H | O | H | Cl | O | H | S | C₂H₅ |
| 3,5-F₂ | O | H | Cl | O | H | O | C₂H₅ |
| 3,5-F₂ | O | H | Br | O | H | O | C₂H₅ |
| 3,5-F₂ | O | H | F | O | H | O | C₂H₅ |
| 3,5-F₂ | O | H | CH₃ | O | H | O | C₂H₅ |
| 2,4-F₂ | O | H | Cl | O | H | O | C₂H₅ |
| 2,4-F₂ | O | H | Br | O | H | O | C₂H₅ |
| 2,4-F₂ | O | H | F | O | H | O | C₂H₅ |
| 2,4-F₂ | O | H | CH₃ | O | H | O | C₂H₅ |
| 3,4-F₂ | O | H | Cl | O | H | O | C₂H₅ |
| 3,4-F₂ | O | H | Br | O | H | O | C₂H₅ |
| 3,4-F₂ | O | H | F | O | H | O | C₂H₅ |
| 3,4-F₂ | O | H | CH₃ | O | H | O | C₂H₅ |
| 2,6-F₂ | O | H | Cl | O | H | O | C₂H₅ |
| 2,6-F₂ | O | H | F | O | H | O | C₂H₅ |
| 2,6-F₂ | O | H | Br | O | H | O | C₂H₅ |

-continued

| | | | | | | | | Ring subst. |
|---|---|---|---|---|---|---|---|---|
| C₂H₅ | o | H | o | CH₃ | H | o | H | 2,6-F₂ |
| C₂H₅ | o | H | o | Cl | H | o | H | 2,5-F₂ |
| C₂H₅ | o | H | o | Br | H | o | H | 2,5-F₂ |
| C₂H₅ | o | H | o | F | H | o | H | 2,5-F₂ |
| C₂H₅ | o | H | o | CH₃ | H | o | H | 2,5-F₂ |
| C₂H₅ | o | H | o | Cl | H | o | H | 2,3-F₂ |
| C₂H₅ | o | H | o | Br | H | o | H | 2,3-F₂ |
| C₂H₅ | o | H | o | F | H | o | H | 2,3-F₂ |
| C₂H₅ | o | H | o | CH₃ | H | o | H | 2,3-F₂ |
| C₂H₅ | o | H | o | Cl | H | o | H | 3,4-Cl₂ |
| C₂H₅ | o | H | o | Br | H | o | H | 3,4-Cl₂ |
| C₂H₅ | o | H | o | F | H | o | H | 3,4-Cl₂ |
| C₂H₅ | o | H | o | CH₃ | H | o | H | 3,4-Cl₂ |
| C₂H₅ | o | H | o | Cl | H | o | H | 3,5-Cl₂ |
| C₂H₅ | o | H | o | Br | H | o | H | 3,5-Cl₂ |
| C₂H₅ | o | H | o | F | H | o | H | 3,5-Cl₂ |
| C₂H₅ | o | H | o | CH₃ | H | o | H | 3,5-Cl₂ |
| C₂H₅ | o | H | o | Cl | H | o | H | 2,4-Cl₂ |
| C₂H₅ | o | H | o | Br | H | o | H | 2,4-Cl₂ |
| C₂H₅ | o | H | o | F | H | o | H | 2,4-Cl₂ |
| C₂H₅ | o | H | o | CH₃ | H | o | H | 2,4-Cl₂ |
| C₂H₅ | o | H | o | Cl | H | o | H | 2,5-Cl₂ |
| C₂H₅ | o | H | o | Br | H | o | H | 2,5-Cl₂ |
| C₂H₅ | o | H | o | F | H | o | H | 2,5-Cl₂ |
| C₂H₅ | o | H | o | CH₃ | H | o | H | 2,5-Cl₂ |
| C₂H₅ | o | H | o | Cl | H | o | H | 2,3-Cl₂ |
| C₂H₅ | o | H | o | Br | H | o | H | 2,3-Cl₂ |
| C₂H₅ | o | H | o | F | H | o | H | 2,3-Cl₂ |
| C₂H₅ | o | H | o | CH₃ | H | o | H | 2,3-Cl₂ |
| C₂H₅ | o | H | o | Cl | H | o | H | 3,5-Br₂ |
| C₂H₅ | o | H | o | F | H | o | H | 3,5-Br₂ |
| C₂H₅ | o | H | o | Br | H | o | H | 3,5-Br₂ |
| C₂H₅ | o | H | o | CH₃ | H | o | H | 3,5-Br₂ |
| C₂H₅ | o | H | o | Cl | H | o | H | 2,3-Br₂ |
| C₂H₅ | o | H | o | F | H | o | H | 2,3-Br₂ |
| C₂H₅ | o | H | o | Br | H | o | H | 2,3-Br₂ |
| C₂H₅ | o | H | o | CH₃ | H | o | H | 2,3-Br₂ |
| C₂H₅ | o | H | o | Cl | H | o | H | 2,5-Br₂ |
| C₂H₅ | o | H | o | F | H | o | H | 2,5-Br₂ |
| C₂H₅ | o | H | o | Br | H | o | H | 2,5-Br₂ |
| C₂H₅ | o | H | o | CH₃ | H | o | H | 2,5-Br₂ |
| C₂H₅ | o | H | o | Cl | H | o | H | 3,4-(CH₃)₂ |
| C₂H₅ | o | H | o | F | H | o | H | 3,4-(CH₃)₂ |
| C₂H₅ | o | H | o | Br | H | o | H | 3,4-(CH₃)₂ |
| C₂H₅ | o | H | o | CH₃ | H | o | H | 3,4-(CH₃)₂ |
| C₂H₅ | o | H | o | Cl | H | o | H | 3,5-(CH₃)₂ |
| C₂H₅ | o | H | o | F | H | o | H | 3,5-(CH₃)₂ |
| C₂H₅ | o | H | o | Br | H | o | H | 3,5-(CH₃)₂ |
| C₂H₅ | o | H | o | CH₃ | H | o | H | 3,5-(CH₃)₂ |
| C₂H₅ | o | H | o | Cl | H | o | H | 2,5-(CH₃)₂ |
| C₂H₅ | o | H | o | F | H | o | H | 2,5-(CH₃)₂ |
| C₂H₅ | o | H | o | Br | H | o | H | 2,5-(CH₃)₂ |
| C₂H₅ | o | H | o | CH₃ | H | o | H | 2,5-(CH₃)₂ |
| C₂H₅ | o | H | o | Cl | H | o | H | 2,3-(CH₃)₂ |

| | | | | | | | |
|---|---|---|---|---|---|---|---|
| 2,3-(CH₃)₂ | O | H | H | F | H | O | C₂H₅ |
| 2,3-(CH₃)₂ | O | H | H | Br | H | O | C₂H₅ |
| 2,3-(CH₃)₂ | O | H | H | CH₃ | H | O | C₂H₅ |
| 3,5-(CF₃)₂ | O | H | H | F | H | O | C₂H₅ |
| 3,5-(CF₃)₂ | O | H | H | Cl | H | O | C₂H₅ |
| 3,5-(CF₃)₂ | O | H | H | Br | H | O | C₂H₅ |
| 3,4,5-Cl₃ | O | H | H | CH₃ | H | O | C₂H₅ |
| 3,4,5-Cl₃ | O | H | H | F | H | O | C₂H₅ |
| 3,4,5-Cl₃ | O | H | H | Cl | H | O | C₂H₅ |
| 2-F, 4-Cl | O | H | H | Br | H | O | C₂H₅ |
| 2-F, 4-Cl | O | H | H | CH₃ | H | O | C₂H₅ |
| 2-F, 4-Cl | O | H | H | F | H | O | C₂H₅ |
| 2-Cl, 4-Cl | O | H | H | Cl | H | O | C₂H₅ |
| 2-Cl, 4-Cl | O | H | H | Br | H | O | C₂H₅ |
| 2-Cl, 4-Cl | O | H | H | CH₃ | H | O | C₂H₅ |
| 2-Cl, 4-Br | O | H | H | F | H | O | C₂H₅ |
| 2-Cl, 4-Br | O | H | H | Cl | H | O | C₂H₅ |
| 2-Cl, 4-Br | O | H | H | Br | H | O | C₂H₅ |
| 2-F, 4-CH₃ | O | H | H | CH₃ | H | O | C₂H₅ |
| 2-F, 4-CH₃ | O | H | H | F | H | O | C₂H₅ |
| 2-F, 4-CH₃ | O | H | H | Cl | H | O | C₂H₅ |
| 2-Cl, 4-CH₃ | O | H | H | Br | H | O | C₂H₅ |
| 2-Cl, 4-CH₃ | O | H | H | CH₃ | H | O | C₂H₅ |
| 2-Cl, 4-CH₃ | O | H | H | F | H | O | C₂H₅ |
| 2,4-Br₂ | O | H | H | Cl | H | O | C₂H₅ |
| 2,4-Br₂ | O | H | H | Br | H | O | C₂H₅ |
| 2,4-Br₂ | O | H | H | CH₃ | H | O | C₂H₅ |
| 2-F, 4-Br | O | H | H | F | H | O | C₂H₅ |
| 2-F, 4-Br | O | H | H | Cl | H | O | C₂H₅ |
| 2-F, 4-Br | O | H | H | Br | H | O | C₂H₅ |
| 2-Cl, 4-CF₃ | O | H | H | CH₃ | H | O | C₂H₅ |
| 2-Cl, 4-CF₃ | O | H | H | F | H | O | C₂H₅ |
| 2-Cl, 4-CF₃ | O | H | H | Cl | H | O | C₂H₅ |
| 2-CF₃, 4-Cl | O | H | H | Br | H | O | C₂H₅ |
| 2-CF₃, 4-Cl | O | H | H | CH₃ | H | O | C₂H₅ |
| 2-CF₃, 4-Cl | O | H | H | F | H | O | C₂H₅ |
| 2-Cl, 4-F | O | H | H | Cl | H | O | C₂H₅ |
| 2-Cl, 4-F | O | H | H | Br | H | O | C₂H₅ |
| 2-Cl, 4-F | O | H | H | CH₃ | H | O | C₂H₅ |
| 2-CF₃, 4-Cl | O | H | H | F | H | O | C₂H₅ |
| 2-CF₃, 4-Cl | O | H | H | Cl | H | O | C₂H₅ |
| 2-CF₃, 4-Cl | O | H | H | Br | H | O | C₂H₅ |
| 2-CH₃, 4-Cl | O | H | H | CH₃ | H | O | C₂H₅ |
| 2-CH₃, 4-Cl | O | H | H | F | H | O | C₂H₅ |
| 2-CH₃, 4-Cl | O | H | H | Cl | H | O | C₂H₅ |
| 2-Br, 4-CH₃ | O | H | H | Br | H | O | C₂H₅ |
| 2-Br, 4-CH₃ | O | H | H | CH₃ | H | O | C₂H₅ |
| 2-Br, 4-CH₃ | O | H | H | F | H | O | C₂H₅ |
| 2-Br, 4-CH₃ | O | H | H | Br | H | O | C₂H₅ |

-continued

| | | | | | | | |
|---|---|---|---|---|---|---|---|
| 2-Br, 4-CH₃ | H | CH₃ | H | O | H | O | C₂H₅ |
| 3-F, 4-CH₃ | H | Cl | H | O | H | O | C₂H₅ |
| 3-F, 4-CH₃ | H | F | H | O | H | O | C₂H₅ |
| 3-F, 4-CH₃ | H | Br | H | O | H | O | C₂H₅ |
| 3-Cl, 4-CH₃ | H | CH₃ | H | O | H | O | C₂H₅ |
| 3-Cl, 4-CH₃ | H | Cl | H | O | H | O | C₂H₅ |
| 3-Cl, 4-CH₃ | H | F | H | O | H | O | C₂H₅ |
| 3-Cl, 4-CH₃ | H | Br | H | O | H | O | C₂H₅ |
| 3-Br, 4-CH₃ | H | CH₃ | H | O | H | O | C₂H₅ |
| 3-Br, 4-CH₃ | H | Cl | H | O | H | O | C₂H₅ |
| 3-Br, 4-CH₃ | H | F | H | O | H | O | C₂H₅ |
| 3-Br, 4-CH₃ | H | Br | H | O | H | O | C₂H₅ |
| 3-CH₃, 4-F | H | CH₃ | H | O | H | O | C₂H₅ |
| 3-CH₃, 4-F | H | Cl | H | O | H | O | C₂H₅ |
| 3-CH₃, 4-F | H | F | H | O | H | O | C₂H₅ |
| 3-CH₃, 4-F | H | Br | H | O | H | O | C₂H₅ |
| 3-CH₃, 4-Br | H | CH₃ | H | O | H | O | C₂H₅ |
| 3-CH₃, 4-Br | H | Cl | H | O | H | O | C₂H₅ |
| 3-CH₃, 4-Br | H | F | H | O | H | O | C₂H₅ |
| 3-CH₃, 4-Br | H | Br | H | O | H | O | C₂H₅ |
| 3-Cl, 4-F | H | CH₃ | H | O | H | O | C₂H₅ |
| 3-Cl, 4-F | H | Cl | H | O | H | O | C₂H₅ |
| 3-Cl, 4-F | H | F | H | O | H | O | C₂H₅ |
| 3-Cl, 4-F | H | Br | H | O | H | O | C₂H₅ |
| 3-F, 4-Cl | H | CH₃ | H | O | H | O | C₂H₅ |
| 3-F, 4-Cl | H | Cl | H | O | H | O | C₂H₅ |
| 3-F, 4-Cl | H | F | H | O | H | O | C₂H₅ |
| 3-F, 4-Cl | H | Br | H | O | H | O | C₂H₅ |
| 3-Cl, 4-Br | H | CH₃ | H | O | H | O | C₂H₅ |
| 3-Cl, 4-Br | H | Cl | H | O | H | O | C₂H₅ |
| 3-Cl, 4-Br | H | F | H | O | H | O | C₂H₅ |
| 3-Cl, 4-Br | H | Br | H | O | H | O | C₂H₅ |
| 3-F, 4-Br | H | CH₃ | H | O | H | O | C₂H₅ |
| 3-F, 4-Br | H | Cl | H | O | H | O | C₂H₅ |
| 3-F, 4-Br | H | F | H | O | H | O | C₂H₅ |
| 3-F, 4-Br | H | Br | H | O | H | O | C₂H₅ |
| 3-CF₃, 4-Cl | H | CH₃ | H | O | H | O | C₂H₅ |
| 3-CF₃, 4-Cl | H | Cl | H | O | H | O | C₂H₅ |
| 3-CF₃, 4-Cl | H | F | H | O | H | O | C₂H₅ |
| 3-CF₃, 4-Cl | H | Br | H | O | H | O | C₂H₅ |
| 3-NO₂, 4-Cl | H | CH₃ | H | O | H | O | C₂H₅ |
| 3-NO₂, 4-Cl | H | Cl | H | O | H | O | C₂H₅ |
| 3-NO₂, 4-Cl | H | F | H | O | H | O | C₂H₅ |
| 3-NO₂, 4-Cl | H | Br | H | O | H | O | C₂H₅ |
| 2-Cl, 5-CH₃ | H | CH₃ | H | O | H | O | C₂H₅ |
| 2-Cl, 5-CH₃ | H | Cl | H | O | H | O | C₂H₅ |
| 2-Cl, 5-CH₃ | H | F | H | O | H | O | C₂H₅ |
| 2-Cl, 5-CH₃ | H | Br | H | O | H | O | C₂H₅ |
| 2-F, 5-CH₃ | H | CH₃ | H | O | H | O | C₂H₅ |
| 2-F, 5-CH₃ | H | Cl | H | O | H | O | C₂H₅ |

| | | | | | | | | |
|---|---|---|---|---|---|---|---|---|
| 2-F, 5-CH₃ | ○ | H | ○ | Br | ○ | H | ○ | C₂H₅ |
| 2-F, 5-CH₃ | ○ | H | ○ | CH₃ | ○ | H | ○ | C₂H₅ |
| 3-CH₃, 4-Cl | ○ | H | ○ | F | ○ | H | ○ | C₂H₅ |
| 3-CH₃, 4-Cl | ○ | H | ○ | Cl | ○ | H | ○ | C₂H₅ |
| 3-CH₃, 4-Cl | ○ | H | ○ | Br | ○ | H | ○ | C₂H₅ |
| 3-CH₃, 4-Cl | ○ | H | ○ | CH₃ | ○ | H | ○ | C₂H₅ |
| 3,5-(CH₃)₂, 4-Cl | ○ | H | ○ | F | ○ | H | ○ | C₂H₅ |
| 3,5-(CH₃)₂, 4-Cl | ○ | H | ○ | Cl | ○ | H | ○ | C₂H₅ |
| 3,5-(CH₃)₂, 4-Cl | ○ | H | ○ | Br | ○ | H | ○ | C₂H₅ |
| 3,5-(CH₃)₂, 4-Cl | ○ | H | ○ | CH₃ | ○ | H | ○ | C₂H₅ |
| 2,3,4-Cl₃ | ○ | H | ○ | F | ○ | H | ○ | C₂H₅ |
| 2,3,4-Cl₃ | ○ | H | ○ | Cl | ○ | H | ○ | C₂H₅ |
| 2,3,4-Cl₃ | ○ | H | ○ | Br | ○ | H | ○ | C₂H₅ |
| 2,3,4-Cl₃ | ○ | H | ○ | CH₃ | ○ | H | ○ | C₂H₅ |
| 2,3,5-Cl₃ | ○ | H | ○ | F | ○ | H | ○ | C₂H₅ |
| 2,3,5-Cl₃ | ○ | H | ○ | Cl | ○ | H | ○ | C₂H₅ |
| 2,3,5-Cl₃ | ○ | H | ○ | Br | ○ | H | ○ | C₂H₅ |
| 2,3,5-Cl₃ | ○ | H | ○ | CH₃ | ○ | H | ○ | C₂H₅ |
| 2,4,6-Cl₃ | ○ | H | ○ | Cl | ○ | H | ○ | C₂H₅ |
| 2,4-Cl₂, 3,5-(CH₃)₂ | ○ | H | ○ | Cl | ○ | H | ○ | C₂H₅ |
| 2,3,5,6-F₅ | ○ | H | ○ | Cl | ○ | H | ○ | C₂H₅ |
| 2,3,4,5,6-F₄ | ○ | H | ○ | Cl | ○ | H | ○ | C₂H₅ |
| H | ○ | H | ○ | Cl | ○ | H | ○ | C₂H₅ |
| H | ○ | H | ○ | Cl | ○ | H | ○ | C₂H₅ |
| H | ○ | 6-Cl | ○ | Cl | ○ | H | ○ | C₂H₅ |
| H | ○ | 6-F | ○ | Cl | ○ | H | ○ | C₂H₅ |
| H | ○ | 3,4-Cl₂ | ○ | Cl | ○ | H | ○ | C₂H₅ |
| H | ○ | 3,4-(CH₃)₂ | ○ | Cl | ○ | H | ○ | C₂H₅ |
| 3-F | ○ | 3-Cl | ○ | Cl | ○ | H | ○ | C₂H₅ |
| 3,5-F₂ | ○ | 5-Cl | ○ | Cl | ○ | H | ○ | C₂H₅ |
| 3-Cl | ○ | 5-Cl | ○ | Cl | ○ | H | ○ | C₂H₅ |
| 3,4-Cl₂ | ○ | 5-Cl | ○ | Cl | ○ | H | ○ | C₂H₅ |
| 4-Cl | ○ | 5-Cl | ○ | Cl | ○ | H | ○ | C₂H₅ |
| 3,5-Cl₂ | ○ | 5-Cl | ○ | Cl | ○ | H | ○ | C₂H₅ |
| 2,4-F₂ | ○ | 5-Cl | ○ | Cl | ○ | H | ○ | C₂H₅ |
| 3,4-F₂ | ○ | 5-Cl | ○ | Cl | ○ | H | ○ | C₂H₅ |
| 4-F | ○ | 5-Cl | ○ | Cl | ○ | H | ○ | C₂H₅ |
| 3-CH₃ | ○ | 5-Cl | ○ | Cl | ○ | H | ○ | C₂H₅ |
| 3,4-(CH₃)₂ | ○ | 5-Cl | ○ | Cl | ○ | H | ○ | C₂H₅ |
| 3-F, 4-CH₃ | ○ | 5-Cl | ○ | Cl | ○ | H | ○ | C₂H₅ |
| 3-F, 4-Cl | ○ | 5-Cl | ○ | Cl | ○ | H | ○ | C₂H₅ |
| 3-CH₃, 4-Cl | ○ | 5-Cl | ○ | Cl | ○ | H | ○ | C₂H₅ |
| 2,5-F₂ | ○ | 5-Cl | ○ | Cl | ○ | H | ○ | C₂H₅ |
| 3,4-F₂ | ○ | 5-Cl | ○ | Cl | ○ | H | ○ | C₂H₅ |
| 3-CH₃, 4-Cl | ○ | 5-Cl | ○ | Cl | ○ | H | ○ | C₂H₅ |
| H | ○ | 5-Br | ○ | Cl | ○ | H | ○ | C₂H₅ |
| 3-F | ○ | 5-Br | ○ | Cl | ○ | H | ○ | C₂H₅ |
| 3,5-F₂ | ○ | 5-Br | ○ | Cl | ○ | H | ○ | C₂H₅ |
| 3-Cl | ○ | 5-Br | ○ | Cl | ○ | H | ○ | C₂H₅ |
| 3,4-Cl₂ | ○ | 5-Br | ○ | Cl | ○ | H | ○ | C₂H₅ |
| 4-Cl | ○ | 5-Br | ○ | Cl | ○ | H | ○ | C₂H₅ |
| 3,5-Cl₂ | ○ | 5-Br | ○ | Cl | ○ | H | ○ | C₂H₅ |
| 2,4-F₂ | ○ | 5-Br | ○ | Cl | ○ | H | ○ | C₂H₅ |
| 3,4-F₂ | ○ | 5-Br | ○ | Cl | ○ | H | ○ | C₂H₅ |

-continued

| | | | | | | | |
|---|---|---|---|---|---|---|---|
| 4-F | o | 5-Br | Cl | o | H | o | C₂H₅ |
| 3-CH₃ | o | 5-Br | Cl | o | H | o | C₂H₅ |
| 3,4-(CH₃)₂ | o | 5-Br | Cl | o | H | o | C₂H₅ |
| 3,5-(CH₃)₂ | o | 5-Br | Cl | o | H | o | C₂H₅ |
| 3-F, 4-CH₃ | o | 5-Br | Cl | o | H | o | C₂H₅ |
| 3-Cl, 4-CH₃ | o | 5-Br | Cl | o | H | o | C₂H₅ |
| 3-F, 4-Cl | o | 5-Br | Cl | o | H | o | C₂H₅ |
| 3-CH₃, 4-Cl | o | 5-Br | Cl | o | H | o | C₂H₅ |
| 2,5-F₂ | o | 5-Br | Cl | o | H | o | C₂H₅ |
| 2,3-F₂ | o | 5-Br | Cl | o | H | o | C₂H₅ |
| 3-CH₃, 4-Cl | o | 5-Br | Cl | o | H | o | C₂H₅ |
| H | o | 5-F | Cl | o | H | o | C₂H₅ |
| 3-F | o | 5-F | Cl | o | H | o | C₂H₅ |
| 3,5-F₂ | o | 5-F | Cl | o | H | o | C₂H₅ |
| 3-Cl | o | 5-F | Cl | o | H | o | C₂H₅ |
| 3,4-Cl₂ | o | 5-F | Cl | o | H | o | C₂H₅ |
| 4-Cl | o | 5-F | Cl | o | H | o | C₂H₅ |
| 3,5-Cl₂ | o | 5-F | Cl | o | H | o | C₂H₅ |
| 2,4-Cl₂ | o | 5-F | Cl | o | H | o | C₂H₅ |
| 3,4-F₂ | o | 5-F | Cl | o | H | o | C₂H₅ |
| 4-F | o | 5-F | Cl | o | H | o | C₂H₅ |
| 3-CH₃ | o | 5-F | Cl | o | H | o | C₂H₅ |
| 3,4-(CH₃)₂ | o | 5-F | Cl | o | H | o | C₂H₅ |
| 3,5-(CH₃)₂ | o | 5-F | Cl | o | H | o | C₂H₅ |
| 3-F, 4-CH₃ | o | 5-F | Cl | o | H | o | C₂H₅ |
| 3-Cl, 4-CH₃ | o | 5-F | Cl | o | H | o | C₂H₅ |
| 3-F, 4-Cl | o | 5-F | Cl | o | H | o | C₂H₅ |
| 3-CH₃, 4-Cl | o | 5-F | Cl | o | H | o | C₂H₅ |
| 2,5-F₂ | o | 5-F | Cl | o | H | o | C₂H₅ |
| 2,3-F₂ | o | 5-F | Cl | o | H | o | C₂H₅ |
| 3-CH₃, 4-Cl | o | 5-F | Cl | o | H | o | C₂H₅ |
| H | o | 5-CH₃ | Cl | o | H | o | C₂H₅ |
| 3-F | o | 5-CH₃ | Cl | o | H | o | C₂H₅ |
| 3,5-F₂ | o | 5-CH₃ | Cl | o | H | o | C₂H₅ |
| 3-Cl | o | 5-CH₃ | Cl | o | H | o | C₂H₅ |
| 3,4-Cl₂ | o | 5-CH₃ | Cl | o | H | o | C₂H₅ |
| 4-Cl | o | 5-CH₃ | Cl | o | H | o | C₂H₅ |
| 3,5-Cl₂ | o | 5-CH₃ | Cl | o | H | o | C₂H₅ |
| 2,4-Cl₂ | o | 5-CH₃ | Cl | o | H | o | C₂H₅ |
| 3,4-F₂ | o | 5-CH₃ | Cl | o | H | o | C₂H₅ |
| 4-F | o | 5-CH₃ | Cl | o | H | o | C₂H₅ |
| 3-CH₃ | o | 5-CH₃ | Cl | o | H | o | C₂H₅ |
| 3,4-(CH₃)₂ | o | 5-CH₃ | Cl | o | H | o | C₂H₅ |
| 3,5-(CH₃)₂ | o | 5-CH₃ | Cl | o | H | o | C₂H₅ |
| 3-F, 4-CH₃ | o | 5-CH₃ | Cl | o | H | o | C₂H₅ |
| 3-Cl, 4-CH₃ | o | 5-CH₃ | Cl | o | H | o | C₂H₅ |
| 3-F, 4-Cl | o | 5-CH₃ | Cl | o | H | o | C₂H₅ |
| 3-CH₃, 4-Cl | o | 5-CH₃ | Cl | o | H | o | C₂H₅ |
| 2,5-F₂ | o | 5-CH₃ | Cl | o | H | o | C₂H₅ |
| 2,3-F₂ | o | 5-CH₃ | Cl | o | H | o | C₂H₅ |
| 3-CH₃, 4-Cl | o | 5-CH₃ | Cl | o | H | o | C₂H₅ |
| H | o | H | Cl | o | H | o | CH₃ |
| H | o | H | Cl | o | H | o | n-C₃H₇ |
| H | o | H | Cl | o | H | o | iso-C₃H₇ |
| H | o | H | Cl | o | H | o | n-C₄H₉ |
| H | o | H | Cl | o | H | o | iso-C₄H₉ |
| H | o | H | Cl | o | H | o | sec-C₄H₉ |

| | | | | | | |
|---|---|---|---|---|---|---|
| H | O | H | Cl | H | O | tert-C₄H₉ |
| H | O | H | Cl | H | O | n-C₅H₁₁ |
| H | O | H | Cl | H | O | c-C₆H₁₃ |
| H | O | H | Cl | H | S | CH₃ |
| 3-F | O | H | Cl | H | O | C₂H₅ |
| 3-F | O | H | Cl | H | S | CH₃ |
| 3-F | O | H | Cl | H | O | n-C₃H₇ |
| 3-F | O | H | Cl | H | O | iso-C₃H₇ |
| 3,5-F₂ | O | H | Cl | H | S | CH₃ |
| 3,5-F₂ | O | H | Cl | H | O | C₂H₅ |
| 3,5-F₂ | O | H | Cl | H | O | n-C₃H₇ |
| 3,5-F₂ | O | H | Cl | H | O | iso-C₃H₇ |
| 4-Cl | O | H | Cl | H | S | CH₃ |
| 4-Cl | O | H | Cl | H | O | C₂H₅ |
| 4-Cl | O | H | Cl | H | O | n-C₃H₇ |
| 4-Cl | O | H | Cl | H | O | iso-C₃H₇ |
| 3,4-Cl₂ | O | H | Cl | H | S | CH₃ |
| 3,4-Cl₂ | O | H | Cl | H | O | C₂H₅ |
| 3,4-Cl₂ | O | H | Cl | H | O | n-C₃H₇ |
| 3,4-Cl₂ | O | H | Cl | H | O | iso-C₃H₇ |
| 2,4-F₂ | O | H | Cl | H | S | CH₃ |
| 2,4-F₂ | O | H | Cl | H | O | C₂H₅ |
| 2,4-F₂ | O | H | Cl | H | O | n-C₃H₇ |
| 2,4-F₂ | O | H | Cl | H | O | iso-C₃H₇ |
| 4-F | O | H | Cl | H | S | CH₃ |
| 4-F | O | H | Cl | H | O | C₂H₅ |
| 4-F | O | H | Cl | H | O | n-C₃H₇ |
| 4-F | O | H | Cl | H | O | iso-C₃H₇ |
| 3-Cl | O | H | Cl | H | S | CH₃ |
| 3-Cl | O | H | Cl | H | O | C₂H₅ |
| 3-Cl | O | H | Cl | H | O | n-C₃H₇ |
| 3-Cl | O | H | Cl | H | O | iso-C₃H₇ |
| H | O | H | Cl | H | O | —CH₂CF₃ |
| H | O | H | Cl | H | O | —CH₂CHCl₂ |
| H | O | H | Cl | H | O | —CH₂CH=CH₂ |
| H | O | H | Cl | H | O | —CH₂C(CH₃)=CH₂ |
| H | O | H | Cl | H | O | —CH₂C(Cl)=CH₂ |
| H | O | H | Cl | H | O | —CH₂C≡CH |
| H | O | H | Cl | H | O | —CH₂C≡C—Cl |
| H | O | H | Cl | H | O | —CH₂CH₂OCH₃ |
| H | O | H | Cl | H | O | ▷ (cyclopropyl) |
| 3-F | O | H | Cl | H | S | CH₃ |

-continued

| | | | | | | | |
|---|---|---|---|---|---|---|---|
| 3-F | O | H | Cl | O | H | O | —CH₂CF₃ |
| 3-F | O | H | Cl | O | H | S | —CH₂CF₃ |
| 3-F | O | H | Cl | O | H | O | ▽ |
| 3-F | O | H | Cl | O | H | S | ▽ |
| 4-F | O | H | Cl | O | H | S | CH₃ |
| 4-F | O | H | Cl | O | H | O | —CH₂CF₃ |
| 4-F | O | H | Cl | O | H | S | —CH₂CF₃ |
| 4-F | O | H | Cl | O | H | O | ▽ |
| 4-F | O | H | Cl | O | H | S | ▽ |
| 3,5-F₂ | O | H | Cl | O | H | S | CH₃ |
| 3,5-F₂ | O | H | Cl | O | H | O | —CH₂CF₃ |
| 3,5-F₂ | O | H | Cl | O | H | S | —CH₂CF₃ |
| 3,5-F₂ | O | H | Cl | O | H | O | ▽ |
| 3,5-F₂ | O | H | Cl | O | H | S | ▽ |
| 2,4-F₂ | O | H | Cl | O | H | S | CH₃ |
| 2,4-F₂ | O | H | Cl | O | H | O | —CH₂CF₃ |
| 2,4-F₂ | O | H | Cl | O | H | S | —CH₂CF₃ |
| 2,4-F₂ | O | H | Cl | O | H | O | ▽ |
| 2,4-F₂ | O | H | Cl | O | H | S | ▽ |
| 3-Cl | O | H | Cl | O | H | S | CH₃ |
| 3-Cl | O | H | Cl | O | H | O | —CH₂CF₃ |
| 3-Cl | O | H | Cl | O | H | S | —CH₂CF₃ |
| 3-Cl | O | H | Cl | O | H | O | ▽ |

-continued

| | | | | | | |
|---|---|---|---|---|---|---|
| 3-Cl | O | H | Cl | O | H | S, △ |
| 4-Cl | O | H | Cl | O | H | O, CH₃ |
| 4-Cl | O | H | Cl | O | H | O, —CH₂CF₃ |
| 4-Cl | O | H | Cl | O | H | S, —CH₂CF₃ |
| 4-Cl | O | H | Cl | O | H | O, △ |
| 4-Cl | O | H | Cl | O | H | S, △ |
| 3,4-Cl₂ | O | H | Cl | O | H | S, CH₃ |
| 3,4-Cl₂ | O | H | Cl | O | H | O, —CH₂CF₃ |
| 3,4-Cl₂ | O | H | Cl | O | H | S, —CH₂CF₃ |
| 3,4-Cl₂ | O | H | Cl | O | H | O, △ |
| 3,4-Cl₂ | O | H | Cl | O | H | S, △ |
| H | O | H | Cl | O | CH₃ | O, C₂H₅ |
| H | —C(=O)— | H | Cl | O | H | O, C₂H₅ |
| 3,4-Cl₂ | CH₂ | H | Cl | O | H | O, C₂H₅ |
| 3,5-F₂ | CH₂ | H | Cl | O | H | O, C₂H₅ |
| H | CH₂ | H | Cl | O | H | O, CH₃ |
| 3-Cl | O | 6-Cl | Cl | O | H | O, C₂H₅ |
| 4-Cl | O | 6-Cl | Cl | O | H | O, C₂H₅ |
| 3-F | O | 6-Cl | Cl | O | H | O, C₂H₅ |
| 4-F | O | 6-Cl | Cl | O | H | O, C₂H₅ |
| H | CH₂ | 5-Cl | Cl | O | H | O, C₂H₅ |
| H | CH₂ | 5-Cl | Cl | O | H | O, CH₃ |
| H | CH₂ | 6-Cl | Cl | O | H | O, C₂H₅ |
| H | CH₂ | 6-Cl | Cl | O | H | O, CH₃ |
| 3-Cl | CH₂ | H | Cl | O | H | O, C₂H₅ |
| 3-Cl | CH₂ | H | Cl | O | H | O, CH₃ |
| 3-F | CH₂ | H | Cl | O | H | O, C₂H₅ |
| 3-F | CH₂ | H | Cl | O | H | O, CH₃ |
| H | CH₂ | H | Cl | O | H | O, CH₂CH₂Cl |
| H | CH₂ | H | Cl | O | H | O, CH₂CHCl₂ |
| H | CH₂ | H | Cl | O | H | O, CH₂CF₃ |
| H | CH₂ | H | Cl | O | H | O, CH₂CCl₃ |

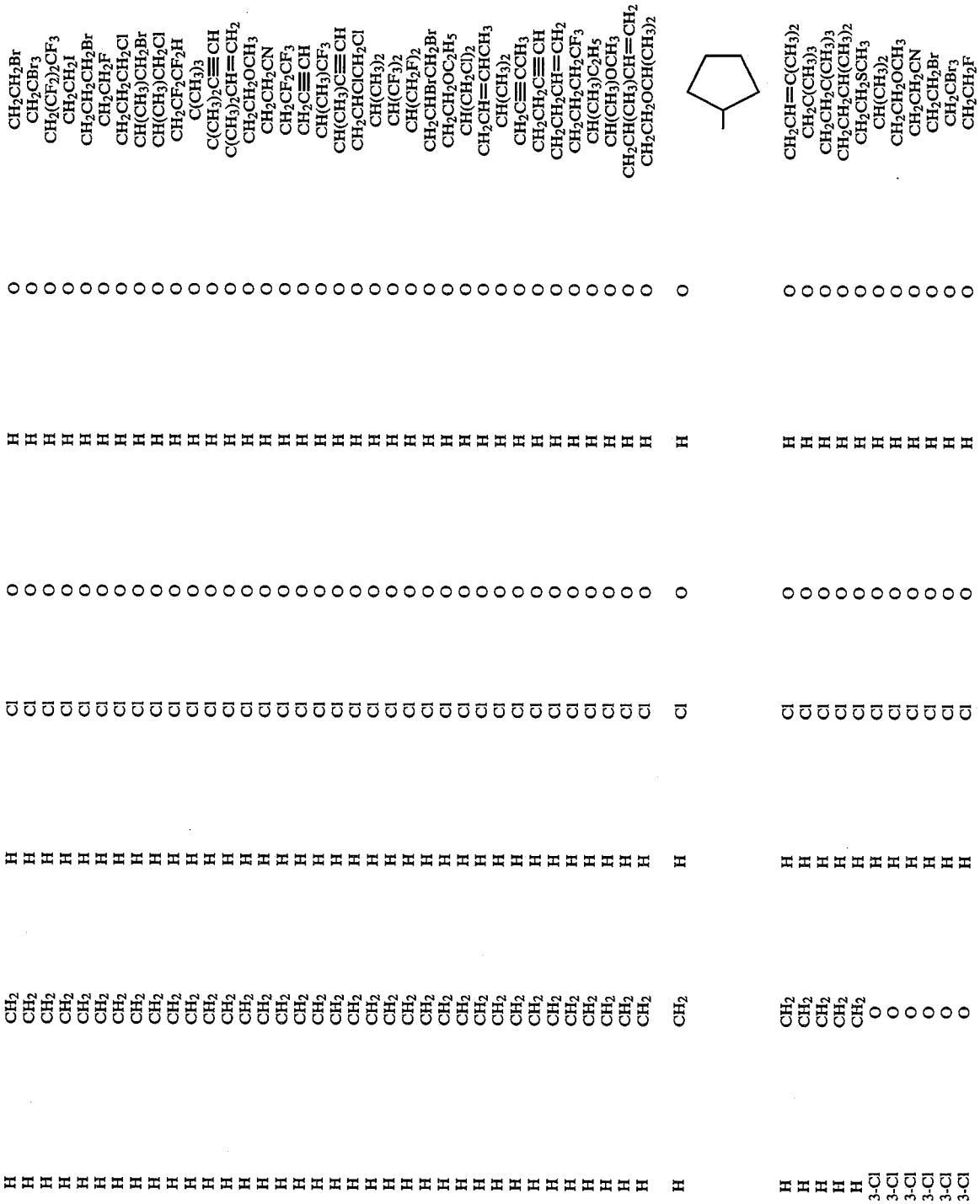

-continued

| X | | | | R |
|---|---|---|---|---|
| 3-Cl | O | H | O | H | O | CH₂CH₂OC₂H₅ |

| X | A | B | C | D | E | R |
|---|---|---|---|---|---|---|
| 3-Cl | O | H | O | H | O | CH₂CH₂OC₂H₅ |
| 3-Cl | O | H | O | H | O | CH(CF₃)₂ |
| 3-Cl | O | H | O | H | O | CH₂CH₂Cl |
| 3-Cl | O | H | O | H | O | CH₂CHCl₂ |
| 3-Cl | O | H | O | H | O | CH₂CCl₃ |
| 3-Cl | O | H | O | H | O | CH₂CF₃ |
| 3-Cl | O | H | O | H | O | CH₂CH₂CH₂Cl |
| 3-Cl | O | H | O | H | O | CH(CH₂Cl)₂ |
| 3-Cl | O | H | O | H | O | CHClCH₂Cl |
| 3-Cl | O | H | O | H | O | CH(CH₃)CH₂Cl |
| 3-Cl | O | H | O | H | O | CH(CH₃)CH₂Br |
| 3-Cl | O | H | O | H | O | CH(CH₂F)₂ |
| 3-Cl | O | H | O | H | O | CH₂CHBrCH₂Br |
| 3-Cl | O | H | O | H | O | CH₂CF₂CF₂H |
| 3-Cl | O | H | O | H | O | CH(CF₃)CH₃ |
| 3-Cl | O | H | O | H | O | CH₂CF₂CF₃ |
| 3-Cl | O | H | O | H | O | CH₂C≡CH |
| 3-Cl | O | H | O | H | O | CH₂CH=CHCH₃ |
| 3-Cl | O | H | O | H | O | CH₂CH(CH₃)₂ |
| 3-Cl | O | H | O | H | O | CH₂C≡CCH₃ |
| 3-Cl | O | H | O | H | O | CH₂C≡CCH₃ |
| 3-Cl | O | H | O | H | O | CH₂CF₂CF₂CF₃ |
| 3-Cl | O | H | O | H | O | CH₂CH₂CH₃CF₃ |
| 3-Cl | O | H | O | H | O | CH₂CH₂CH=CH₂ |
| 3-Cl | O | H | O | H | O | CH(CH₃)CH=CH₂ |
| 3-Cl | O | H | O | H | O | CH(CH₃)C≡CH |
| 3-Cl | O | H | O | H | O | CH(CH₃)₂C≡CH |
| 3-Cl | O | H | O | H | O | CH₂CH₂OCH(CH₃)₂ |
| 3-Cl | O | H | O | H | O | 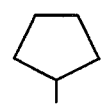 |
| 3-Cl | O | H | O | H | O | C(CH₃)₂CH=CH₂ |
| 3-Cl | O | H | O | H | O | CH₂CH=C(CH₃)₂ |
| 3-Cl | O | H | O | H | O | CH₂C(CH₃)₃ |
| 3-Cl | O | H | O | H | O | CH₂CH₂C(CH₃)₂ |
| 3-Cl | O | H | O | H | O | CH₂CH₂CH(CH₃)₂ |
| 3-Cl | O | H | O | H | O | CH₂CH₂I |
| 3,5-F₂ | O | H | O | H | O | CH₂CH₂SCH₃ |
| 3,5-F₂ | O | H | O | H | O | CH₂CHCl₂ |
| 3,5-F₂ | O | H | O | H | O | CH(CH₂F)₂ |
| 3,5-F₂ | O | H | O | H | O | CH₂CHBrCH₂Br |
| 3,5-F₂ | O | H | O | H | O | CH₂CH₂OC₂H₅ |
| 3,5-F₂ | O | H | O | H | O | CH(CF₃)₂ |
| 3,5-F₂ | O | H | O | H | O | CH₂CF₂CF₂H |
| 3,5-F₂ | O | H | O | H | O | CH(CH₃)CF₃ |
| 3,5-F₂ | O | H | O | H | O | CH₂C₂F₅ |
| 3,5-F₂ | O | H | O | H | O | CH₂C≡CH |
| 3,5-F₂ | O | H | O | H | O | CH₂CH=CH(CH₃) |

-continued

| X | W | R1 | Y | Z | R2 | R3 |
|---|---|----|---|---|----|----|
| 3,5-F$_2$ | O | H | Cl | O | H | CH$_2$CH(CH$_3$)$_2$ |
| 3,5-F$_2$ | O | H | Cl | O | H | CH$_2$CH$_2$C≡CH |
| 3,5-F$_2$ | O | H | Cl | O | H | CH$_2$C≡CCH$_3$ |
| 3,5-F$_2$ | O | H | Cl | O | H | CH$_2$CF$_2$CF$_2$CF$_3$ |
| 3,5-F$_2$ | O | H | Cl | O | H | CH$_2$CH$_2$CH=CH$_2$ |
| 3,5-F$_2$ | O | H | Cl | O | H | CH$_2$CH$_2$C$_2$H$_5$ |
| 3,5-F$_2$ | O | H | Cl | O | H | CH(CH$_3$)C$_2$H$_5$ |
| 3,5-F$_2$ | O | H | Cl | O | H | CH(CH$_3$)OCH$_3$ |
| 3,5-F$_2$ | O | H | Cl | O | H | CH$_2$CCl$_3$ |
| 3,5-F$_2$ | O | H | Cl | O | H | CH$_2$CH$_2$Cl |
| 3,5-F$_2$ | O | H | Cl | O | H | CH$_2$CF$_3$ |
| 3,5-F$_2$ | O | H | Cl | O | H | CH$_2$CH$_2$CH$_2$Cl |
| 3,5-F$_2$ | O | H | Cl | O | H | CH(CH$_3$)CH$_2$Br |
| 3-Cl | O | H | Cl | O | H | C(CH$_3$)$_3$ |
| 4-CH$_2$CF$_3$ | O | H | Cl | O | H | C$_2$H$_5$ |
| 4-CH$_2$C$_2$F$_5$ | O | H | Cl | O | H | C$_2$H$_5$ |
| 3-OCH(CH$_3$)$_2$ | O | H | Cl | O | H | C$_2$H$_5$ |
| 3-OCF$_2$CF$_2$Br | O | H | Cl | O | H | C$_2$H$_5$ |
| 4-OCH$_2$C$_2$H$_5$ | O | H | Cl | O | H | C$_2$H$_5$ |
| H | O | H | Cl | O | H | C$_2$H$_5$ |
| H | O | H | Cl | O | H | C$_2$H$_5$ |
| H | O | H | Cl | O | H | C$_2$H$_5$ |
| 3,5-F$_2$ | O | H | Cl | O | C$_2$H$_5$ | CH$_3$ |
| 3,5-F$_2$ | O | H | Cl | O | n-C$_3$H$_7$ | C$_2$H$_5$ |
| H | O | H | Cl | O | CH$_2$CH$_2$CF$_3$ | C$_2$H$_5$ |
| 3-Cl | O | H | Cl | S | H | C$_2$H$_5$ |
| 3-Cl | O | H | Cl | S | H | CH$_3$ |
| H | CH$_2$ | H | Cl | S | H | C$_2$H$_5$ |
| H | CH$_2$ | H | Cl | S | H | C$_2$H$_5$ |
| H | O | H | Cl | S | H | CH$_3$ |
| H | O | H | Cl | O | H | C$_2$H$_5$ |

| X | W | R1 | Y | Z | R2 | R3 |
|---|---|----|---|---|----|----|
| H | O | H | Cl | O | H | 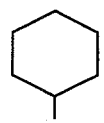 |

| X | W | R1 | Y | Z | R2 | R3 |
|---|---|----|---|---|----|----|
| H | O | H | Cl | O | H | CH$_2$(CH$_2$)$_2$CH=CHCH$_3$ |
| H | O | H | Cl | O | H | CH$_2$CH$_2$O(CH$_2$)$_3$CH$_3$ |
| H | O | H | Cl | O | H | CH$_2$(CH$_2$)$_4$CH$_2$Cl |
| H | O | H | Cl | O | H | CH$_2$C≡CCH$_2$CH$_2$CH$_3$ |
| H | O | H | Cl | O | H | CH$_2$CH=CHCH$_2$Cl |
| H | O | H | Cl | O | H | CH$_2$C≡C—Cl |
| H | O | H | Cl | O | H | CH$_2$CH$_2$C≡C—Cl |

TABLE 2

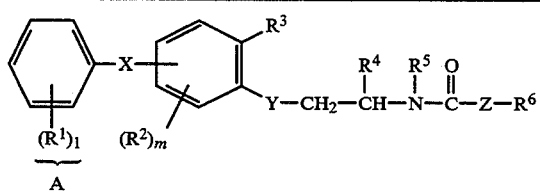

(II) $R^5$ is a hydrogen atom and A is present at the 5-position.

| $(R^1)_l$ | X | $(R^2)_m$ | $R^3$ | Y | $R^4$ | Z | $R^6$ |
|---|---|---|---|---|---|---|---|
| H | O | H | Cl | O | H | O | $C_2H_5$ |
| H | O | H | Br | O | H | O | $C_2H_5$ |
| H | O | H | F | O | H | O | $CH_3$ |
| H | O | H | $CH_3$ | O | H | O | $CH_3$ |
| 3-F | O | H | Cl | O | H | O | $C_2H_5$ |
| 3-F | O | H | F | O | H | O | $CH_3$ |
| 3-F | O | H | Br | O | H | O | $CH_3$ |
| 3-F | O | H | $CH_3$ | O | H | O | $C_2H_5$ |
| 4-F | O | H | Cl | O | H | O | $C_2H_5$ |
| 2-F | O | H | Cl | O | H | O | $CH_3$ |
| 2-Cl | O | H | Cl | O | H | O | $C_2H_5$ |
| 3-Cl | O | H | Cl | O | H | O | $CH_3$ |
| 3-Cl | O | H | Br | O | H | O | $C_2H_5$ |
| 3-Cl | O | H | F | O | H | O | $C_2H_5$ |
| 3-Cl | O | H | $CH_3$ | O | H | O | $CH_3$ |
| 4-Cl | O | H | Cl | O | H | O | $C_2H_5$ |
| 4-Br | O | H | Cl | O | H | O | $CH_3$ |
| 3-Br | O | H | Cl | O | H | O | $C_2H_5$ |
| 2-Br | O | H | Cl | O | H | O | $C_2H_5$ |
| 3-$CH_3$ | O | H | Cl | O | H | O | $CH_3$ |
| 4-$CH_3$ | O | H | Cl | O | H | O | $CH_3$ |
| 3-$CF_3$ | O | H | Cl | O | H | O | $C_2H_5$ |
| 2-$CH_3$ | O | H | Cl | O | H | O | $CH_3$ |
| 3-I | O | H | Cl | O | H | O | $CH_3$ |
| 4-I | O | H | Cl | O | H | O | $C_2H_5$ |
| 3-$OCH_3$ | O | H | Cl | O | H | O | $C_2H_5$ |
| 4-$OCHF_2$ | O | H | Cl | O | H | O | $C_2H_5$ |
| 4-$CF_3$ | O | H | Cl | O | H | O | $C_2H_5$ |
| 3,5-$F_2$ | O | H | Cl | O | H | O | $C_2H_5$ |
| 3,5-$F_2$ | O | H | Br | O | H | O | $C_2H_5$ |
| 3,5-$F_2$ | O | H | F | O | H | O | $C_2H_5$ |
| 3,5-$(CH_3)_2$, 4-Cl | O | H | Cl | O | H | O | $CH_3$ |
| 2,3,4-$Cl_3$ | O | H | Cl | O | H | O | $C_2H_5$ |
| 2,4,5-$Cl_3$ | O | H | Cl | O | H | O | $CH_3$ |
| 2,4,5-$Cl_3$ | O | H | F | O | H | O | $CH_3$ |
| 2,4,5-$Cl_3$ | O | H | Br | O | H | O | $CH_3$ |
| 2,4,5-$Cl_3$ | O | H | $CH_3$ | O | H | O | $CH_3$ |
| 3,5-$F_2$ | O | H | Cl | O | H | O | $CH_3$ |
| 3,4-$Cl_2$ | O | H | Cl | O | H | O | $CH_3$ |
| 3,5-$Cl_2$ | O | H | Cl | O | H | O | $C_2H_5$ |
| 2,4-$F_2$ | O | H | Cl | O | H | O | $CH_3$ |
| 3,4-$F_2$ | O | H | Cl | O | H | O | $CH_3$ |
| 2,4-$Cl_2$ | O | H | Cl | O | H | O | $C_2H_5$ |
| 3,4-$(CH_3)_2$ | O | H | Cl | O | H | O | $C_2H_5$ |
| 3,5-$(CH_3)_2$ | O | H | Cl | O | H | O | $C_2H_5$ |
| 3,5-$Br_2$ | O | H | Cl | O | H | O | $CH_3$ |

TABLE 2-continued

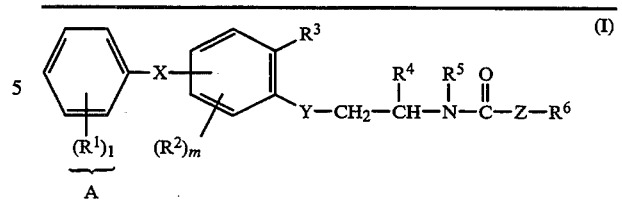

(II) $R^5$ is a hydrogen atom and A is present at the 5-position.

| $(R^1)_l$ | X | $(R^2)_m$ | $R^3$ | Y | $R^4$ | Z | $R^6$ |
|---|---|---|---|---|---|---|---|
| 2,6-$F_2$ | O | H | Cl | O | H | O | $C_2H_5$ |
| 2,5-$Cl_2$ | O | H | Cl | O | H | O | $C_2H_5$ |
| 2,5-$F_2$ | O | H | Cl | O | H | O | $C_2H_5$ |
| 2,5-$(CH_3)_2$ | O | H | Cl | O | H | O | $C_2H_5$ |
| 2,3-$F_2$ | O | H | Cl | O | H | O | $CH_3$ |
| 2,3-$Cl_2$ | O | H | Cl | O | H | O | $C_2H_5$ |
| 2,3-$(CH_3)_2$ | O | H | Cl | O | H | O | $CH_3$ |
| 3,4-$Br_2$ | O | H | Cl | O | H | O | $C_2H_5$ |
| 2,5-$Br_2$ | O | H | Cl | O | H | O | $C_2H_5$ |
| 3,5-$(CH_3)_2$ | O | H | Cl | O | H | O | $C_2H_5$ |
| 3,4,5-$Cl_3$ | O | H | Cl | O | H | O | $CH_3$ |
| 2-F, 4-Cl | O | H | Cl | O | H | O | $CH_3$ |
| 2-Cl, 4-Br | O | H | Cl | O | H | O | $C_2H_5$ |
| 2-Cl, 4-$CH_3$ | O | H | Cl | O | H | O | $C_2H_5$ |
| 3-F, 4-$CH_3$ | O | H | Cl | O | H | O | $C_2H_5$ |
| 2,4-$Br_2$ | O | H | Cl | O | H | O | $C_2H_5$ |
| 2-F, 4-Br | O | H | Cl | O | H | O | $C_2H_5$ |
| 2-Cl, 4-$CF_3$ | O | H | Cl | O | H | O | $C_2H_5$ |
| 2-Cl, 4-F | O | H | Cl | O | H | O | $C_2H_5$ |
| 2-$CF_3$, 4-Cl | O | H | Cl | O | H | O | $CH_3$ |
| 2-$CH_3$, 4-Cl | O | H | Cl | O | H | O | $CH_3$ |
| 2-Br, 4-$CH_3$ | O | H | Cl | O | B | O | $CH_3$ |
| 3-F, 4-$CH_3$ | O | H | Cl | O | H | O | $C_2H_5$ |
| 3-Cl, 4-$CH_3$ | O | H | Cl | O | H | O | $C_2H_5$ |
| 3-Br, 4-$CH_3$ | O | H | Cl | O | H | O | $CH_3$ |
| 3-$CH_3$, 4-F | O | H | Cl | O | H | O | $CH_3$ |
| 3-$CH_3$, 4-Br | O | H | Cl | O | H | O | $C_2H_5$ |
| 3-Cl, 4-F | O | H | Cl | O | H | O | $CH_3$ |
| 3-F, 4-Cl | O | H | cl | O | H | O | $CH_3$ |
| 3-F, 4-Br | O | H | Cl | O | H | O | $CH_3$ |
| 3-Cl, 4-Br | O | H | Cl | O | H | O | $CH_3$ |
| 3-$CF_3$, 4-Cl | O | H | Cl | O | H | O | $C_2H_5$ |
| 2-Cl, 5-$CH_3$ | O | H | Cl | O | H | O | $CH_3$ |
| 2-F, 5-$CH_3$ | O | H | Cl | O | H | O | $CH_3$ |
| 3-$CH_3$, 4-Cl | O | H | Cl | O | H | O | $CH_3$ |
| 3,5-$(CH_3)_2$, 4-Cl | O | H | Cl | O | H | O | $CH_3$ |
| 3,4,5-$Cl_3$ | O | H | Cl | O | H | O | $C_2H_5$ |
| 2,4,5-$Cl_3$ | O | H | Cl | O | H | O | $C_2H_5$ |
| 2,4,6-$Cl_3$ | O | H | Cl | O | H | O | $C_2H_5$ |
| H | O | 6-Cl | Cl | O | H | O | $C_2H_5$ |
| H | O | 6-F | Cl | O | H | O | $C_2H_5$ |
| H | O | 3,4-$Cl_2$ | Cl | O | H | O | $C_2H_5$ |
| H | O | 3,4-$(CH_3)_2$ | Cl | O | H | O | $C_2H_5$ |
| H | O | 3-Cl | Cl | O | H | O | $C_2H_5$ |
| 3,4-$Cl_2$ | O | H | Cl | O | H | O | $C_2H_5$ |
| 3,5-$F_2$ | O | H | Cl | O | H | O | $C_2H_5$ |

TABLE 3

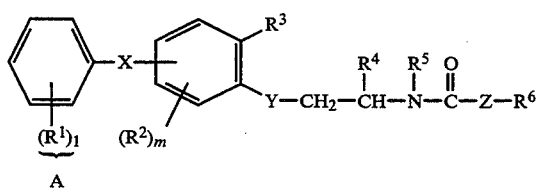

(III) $R^5$ is a group of the formula: $-S(O)_n-N\begin{smallmatrix}R^7\\R^8\end{smallmatrix}$ and A is present at the 4-position.

| $(R^1)_l$ | X | $(R^2)_m$ | $R^3$ | Y | $R^4$ | n | $R^7$ | $R^8$ | Z | $R^6$ |
|---|---|---|---|---|---|---|---|---|---|---|
| H | O | H | Cl | O | H | 0 | $CH_3$ | n-$C_3H_7$ | O | $C_2H_5$ |

TABLE 3-continued $$\underset{A}{\underbrace{\text{Ph}(R^1)_l}}-X-\underset{(R^2)_m}{\text{Ar}(R^3)}-Y-CH_2-\overset{R^4}{\underset{|}{CH}}-\overset{R^5}{\underset{|}{N}}-\overset{O}{\underset{||}{C}}-Z-R^6 \quad (I)$$

(III) $R^5$ is a group of the formula: $-S(O)_n-N\begin{smallmatrix}R^7\\R^8\end{smallmatrix}$ and A is present at the 4-position.

| $(R^1)_l$ | X | $(R^2)_m$ | $R^3$ | Y | $R^4$ | n | $R^7$ | $R^8$ | Z | $R^6$ |
|---|---|---|---|---|---|---|---|---|---|---|
| 3,5-F$_2$ | O | H | Cl | O | H | 0 | C$_2$H$_5$ | n-C$_4$H$_9$ | O | C$_2$H$_5$ |
| H | O | H | Cl | O | H | 0 | n-C$_3$H$_7$ | —CH$_2$CH=CH$_2$ | O | C$_2$H$_5$ |
| H | O | H | Cl | O | H | 0 | n-C$_4$H$_9$ | cyclopropyl | O | C$_2$H$_5$ |
| H | O | H | Cl | O | H | 0 | —CH$_2$CH=CH$_2$ | CH$_3$ | O | CH$_3$ |
| H | O | H | Cl | O | H | 0 | cyclopropyl | C$_2$H$_5$ | O | CH$_3$ |
| H | O | H | Cl | O | H | 0 | —CH$_2$C$_6$H$_5$ | C$_2$H$_5$ | O | CH$_3$ |
| H | O | H | Cl | O | H | 0 | n-C$_5$H$_{11}$ | n-C$_5$H$_{11}$ | O | CH$_3$ |
| H | O | H | Cl | O | H | 0 | n-C$_6$H$_{13}$ | n-C$_6$H$_{13}$ | O | CH$_3$ |
| H | O | H | Cl | O | H | 0 | cyclohexyl | cyclohexyl | O | C$_2$H$_5$ |
| 3-F | O | H | Cl | O | H | 0 | C$_2$H$_5$ | n-C$_3$H$_7$ | O | C$_2$H$_5$ |
| 3,4-Cl$_2$ | O | H | Cl | O | H | 0 | CH$_3$ | n-C$_4$H$_9$ | O | CH$_3$ |
| H | O | H | Cl | O | H | 1 | C$_2$H$_5$ | n-C$_4$H$_9$ | O | CH$_3$ |
| H | O | H | Cl | O | H | 1 | CH$_3$ | n-C$_4$H$_9$ | O | C$_2$H$_5$ |
| H | O | H | Cl | O | H | 2 | C$_2$H$_5$ | n-C$_4$H$_9$ | O | C$_2$H$_5$ |

TABLE 4

$$\underset{A}{\underbrace{\text{Ph}(R^1)_l}}-X-\underset{(R^2)_m}{\text{Ar}(R^3)}-Y-CH_2-\overset{R^4}{\underset{|}{CH}}-\overset{R^5}{\underset{|}{N}}-\overset{O}{\underset{||}{C}}-Z-R^6 \quad (I)$$

(IV) $R^5$ is a group of the formula:

$$-S(O)_n-N\begin{smallmatrix}R^7\\(CH_2)_p-\overset{O}{\underset{||}{C}}-OR_{11}\end{smallmatrix}$$ and A is at the 4-position.

| $(R^1)_l$ | X | $(R^2)_m$ | $R^3$ | Y | $R^4$ | n | $R^7$ | p | $R^{11}$ | Z | $R^6$ |
|---|---|---|---|---|---|---|---|---|---|---|---|
| 4-Cl | O | H | Cl | O | H | 0 | CH$_3$ | 0 | C$_2$H$_5$ | O | C$_2$H$_5$ |
| 3,4-Cl$_2$ | O | H | Cl | O | H | 0 | CH$_3$ | 0 | CH$_3$ | O | C$_2$H$_5$ |
| 3,5-F$_2$ | O | H | Cl | O | H | 0 | C$_2$H$_5$ | 0 | C$_2$H$_5$ | O | C$_2$H$_5$ |
| 3-F | O | H | Cl | O | H | 0 | C$_2$H$_5$ | 0 | CH$_3$ | O | C$_2$H$_5$ |
| H | O | H | Cl | O | H | 0 | C$_2$H$_5$ | 0 | n-C$_3$H$_7$ | O | C$_2$H$_5$ |
| H | O | H | Cl | O | H | 0 | C$_2$H$_5$ | 0 | n-C$_4$H$_9$ | O | C$_2$H$_5$ |
| H | O | H | Cl | O | H | 1 | C$_2$H$_5$ | 0 | C$_2$H$_5$ | O | C$_2$H$_5$ |
| H | O | H | Cl | O | H | 2 | C$_2$H$_5$ | 0 | C$_2$H$_5$ | O | C$_2$H$_5$ |
| H | O | H | Cl | O | H | 0 | C$_2$H$_5$ | 1 | C$_2$H$_5$ | O | C$_2$H$_5$ |
| H | O | H | Cl | O | H | 0 | C$_2$H$_5$ | 2 | C$_2$H$_5$ | O | C$_2$H$_5$ |
| H | O | H | Cl | O | H | 0 | C$_2$H$_5$ | 3 | C$_2$H$_5$ | O | C$_2$H$_5$ |
| H | O | H | Cl | O | H | 0 | C$_2$H$_5$ | 4 | CH$_3$ | O | C$_2$H$_5$ |

TABLE 4-continued

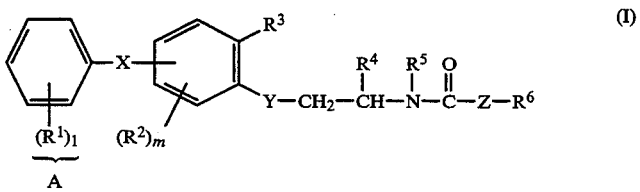

(IV) $R^5$ is a group of the formula:

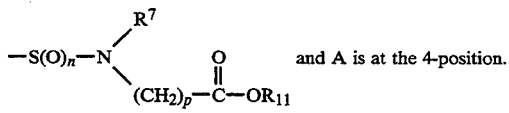

and A is at the 4-position.

| $(R^1)_l$ | X | $(R^2)_m$ | $R^3$ | Y | $R^4$ | \multicolumn{4}{c}{$R^5$} | Z | $R^6$ |
|---|---|---|---|---|---|---|---|---|---|---|---|
| | | | | | | n | $R^7$ | p | $R^{11}$ | | |
| H | O | H | Cl | O | H | 0 | $C_2H_5$ | 5 | $C_2H_5$ | O | $C_2H_5$ |
| H | O | H | Cl | O | H | 0 | $C_2H_5$ | 6 | $CH_3$ | O | $C_2H_5$ |
| H | O | H | Cl | O | H | 0 | $C_2H_5$ | 0 | n-$C_5H_{11}$ | O | $C_2H_5$ |
| H | O | H | Cl | O | H | 0 | $C_2H_5$ | 0 | n-$C_6H_{13}$ | O | $C_2H_5$ |

TABLE 5

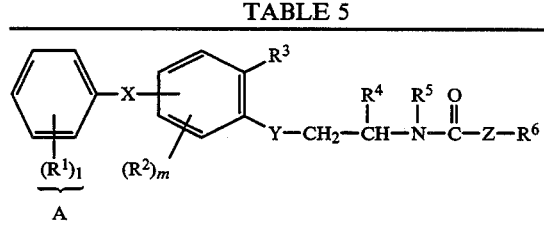

(V) $R^5$ is a group of the formula:

and A is at the 4-position.

| $(R^1)_l$ | X | $(R^2)_m$ | $R^3$ | Y | $R^4$ | $R^5 (= R^9)$ | Z | $R^6$ |
|---|---|---|---|---|---|---|---|---|
| H | O | H | Cl | O | H | H | O | $C_2H_5$ |
| H | O | H | Cl | O | H | 2-F | O | $C_2H_5$ |
| H | O | H | Cl | O | H | 3-Cl | O | $C_2H_5$ |
| H | O | H | Cl | O | H | 4-Br | O | $C_2H_5$ |
| H | O | H | Cl | O | H | 4-I | O | $C_2H_5$ |
| 3-F | O | H | Cl | O | H | H | O | $C_2H_5$ |
| 3,5-$F_2$ | O | H | Cl | O | H | 3-F | O | $C_2H_5$ |
| 4-F | O | H | Cl | O | H | 2-Cl | O | $C_2H_5$ |
| 3-Cl | O | H | Cl | O | H | 2-Br | O | $C_2H_5$ |
| 3,4-$Cl_2$ | O | H | Cl | O | H | H | O | $C_2H_5$ |
| 4-Cl | O | H | Cl | O | H | 3-F | O | $C_2H_5$ |
| 2,4-$F_2$ | O | H | Cl | O | H | 4-Cl | O | $C_2H_5$ |

TABLE 6

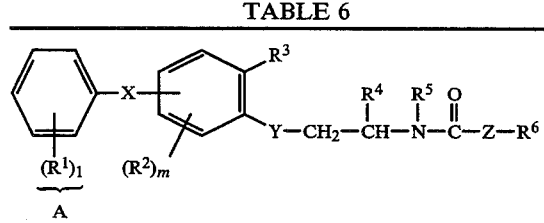

(V) $R^5$ is a group of the formula: $-\overset{\overset{O}{\|}}{C}-\overset{\overset{O}{\|}}{C}-OR^{10}$
and A is at the 4-position.

| $(R^1)_l$ | X | $(R^2)_m$ | $R^3$ | Y | $R^4$ | $R^5 (= R^{10})$ | Z | $R^6$ |
|---|---|---|---|---|---|---|---|---|
| 3,4-$Cl_2$ | O | H | Cl | O | H | $CH_2$ | O | $C_2H_5$ |
| 3,5-$F_2$ | O | H | Cl | O | H | $C_2H_5$ | O | $C_2H_5$ |
| H | O | H | Cl | O | H | n-$C_3H_7$ | O | $C_2H_5$ |
| H | O | H | Cl | O | H | n-$C_4H_9$ | O | $C_2H_5$ |
| H | O | H | Cl | O | H | n-$C_5H_{11}$ | O | $C_2H_5$ |

TABLE 6-continued

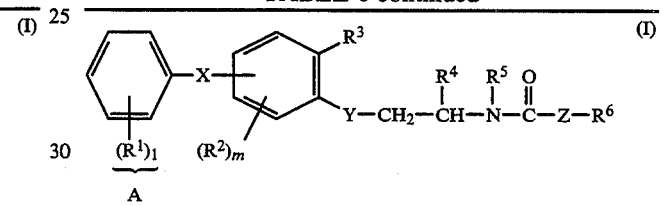

(V) $R^5$ is a group of the formula: $-\overset{\overset{O}{\|}}{C}-\overset{\overset{O}{\|}}{C}-OR^{10}$
and A is at the 4-position.

| $(R^1)_l$ | X | $(R^2)_m$ | $R^3$ | Y | $R^4$ | $R^5 (= R^{10})$ | Z | $R^6$ |
|---|---|---|---|---|---|---|---|---|
| 3,5-$Cl_2$ | O | H | Cl | O | H | $CH_3$ | O | $C_2H_5$ |
| H | O | H | Cl | O | H | n-$C_6H_{13}$ | O | $C_2H_5$ |
| H | O | H | Cl | O | H | n-$C_7H_{15}$ | O | $C_2H_5$ |
| H | O | H | Cl | O | H | n-$C_{10}H_{21}$ | O | $C_2H_5$ |

Examples of the insect pests against which the carbamic acid derivatives (I) exhibit a controlling effect are as follows:

Hemiptera:

Planthoppers such as brown planthopper (*Nilaparvata lugens*), white-backed rice planthopper (*Sogatella furcifera*) and small brown planthopper (*Laodelphax striatellus*); leafhoppers such as green rice leafhopper (*Nephotettix cincticeps*), *Nephotettix virescense*, *Nephotettix nigropictus*, zig-zag rice leafhopper (*Recilia dorsalis*), tea green leafhopper (*Empoasca onukii*) and grape leafhopper (*Arboridia apicalis*); aphids such as cotton aphid (*Aphis gossypii*) and green peach aphid (*Myzus persicae*); bugs; whiteflies (Aleyrodidae) such as sweet potato whitefly (*Bemisia tabaci*) and greenhouse whitefly (*Trialeurodes vaporariorum*); scales; mealy bugs; lace bugs (*Tingidae*); psyllids (Psyllidae), etc.

Lepidoptera:

Pyralid moths (Pyralidae) such as rice stem borer (*Chilo suppressalis*), rice leafroller (*Cnaphalocrocis medinalis*) and Indian meal moth (*Plodia interpunctella*); Noctuidae such as tobacco curworm (*Spodoptera litura*), rice armyworm (*Pseudaletia separate*), cabbage armyworm (*Mamestra brassicae*) and beet semi-looper (*Autographa nigrisigna*); Agrothis spp. such as turnip cutworm (*Agrothis segetum*) and black cutworm (*Agrothis ipsilon*); Hellothis spp.; Pieridae such as common cabbageworm (*Pieris rapae crucivora*); tortricid moths (Tortricidae) such as Adoxophyes spp. and Grapholita spp.; Carposinidae such as lyonetiid moths (Lyonetiidae), leaf-blotch miners (Gracillariidae), gelechiid moths (Gelechiidae) and tussock moths (Lymantriidae); diamondback moth (*Plutella xylostella*), clothes moths (Tineidae), casemaking clothes moth (*Tinea translucens*) and webbing clothes moth (*Tineola bissellleila*), etc.

Diptera:

Mosquitos (Calicidae) such as common mosquito (*Culex pipiens pallens*) and *Culex tritaeniorhynchus*; Aedes spp. such as *Aedes aegypti* and *Aedes albopictus*; Anopheles spp. such as *Anopheles sinensis*; midges (Chironomidae); Muscidae such as housefly (*Musca domestica*) and false stablefly (*Muscina stabulans*); Calliphoridae; Sarcophagidae; lesser housefly (*Fannia canicularis*); anthomyiid flies (Anthomyiidae) such as seedcorn maggot (*Delia platura*) and onion maggot (*Delia antique*); fruit flies (Tephritidae); shore flies (Ephydridae); small fruit flies (Drosophilidae); moth flies (Psychodidae); black flies (Simuliidae); Tabanidae; stable flies (Stomoxyidae); etc.

Coleoptera:

Leaf beetles (Chrysomelidae) such as cucurbit beetle (*Aulacophora femoralis*), striped flea beetles (*Phyllotrata striolata*), western corn rootworm (*Diabrotica virgifora*) and southern corn root worm (*Diabrotica undecimpunctata*); scarabs (Scarabaeidae) such as cupreous chafer (*Anomala cuprea*) and soybeen beetle (*Anomala rufocuprea*); weevils (Cureulionidae) such as maize weevil (*Sitophilus zeamais*), rice water weevil (*Lissorhoptrus oryzophilus*) and adzuki bean weevil (*Callosobruchys chineneis*), etc.; darkling beetles (Tenebrionidae) such as yellow mealworm (*Tenebrio moliter*) and red flour beetles (*Tribolium castaneum*); Anobiidae; Coccinellidae such as twenty-eight-spotted ladybirds (*Epilachna vigintioctopunctata*); powderpost beetles (Lyctidae); false powderpost beetles (Bostrychidae); Cerambysidae, etc.

Dictyoptera:

Blattellidae such as German cockroach (*Blattella germanica*); Blattidae such as smokybrown cockroach (*Periplaneta fuliginosa*), American cockroach (*Periplaneta americana*), brown cockroach (*Periplaneta brunnea*) and oriental cockroach (*Blatta orientalis*), etc.

Thysanoptera:

Thrips such as *Thrips palmi*, yellow tea thrips (*Scirtothrips dorsalis*) and flower thrips (*Thrips hawaiiensis*), etc.

Hymenoptera:

Ants (Formicidae); sawflies (Tenthredinidae) such as cabbage sawfly (*Athalia rosae ruficornis*), etc.

Orthoptera:

Mole crickets (Gryllotalpidae); grasshoppers (Acrididae), etc.

Aphaniptera:

*Purex irritans*, etc.

Anoplura:

*Pediculus humanus capitis, Phthirus pubis*, etc.

Isoptera:

*Reticulitermes speratus*, Formosan subterrauean termite (*Coptotermes formosanus*), etc.

Among the insect pests as above exemplified, the carbamic acid derivatives (I) are particularly effective in controlling those belonging to Hemiptera. They exhibit a noticeable insecticidal activity especially against planthoppers and leafhoppers in a field of rice plant.

In order to control the growth of the insect pests as above exemplified, the carbamic acid derivatives (I) of the invention may be used as such, i.e. without admixing with any other component. For the practical usage, they are normally admixed with any additive(s) as conventionally used in the related art field to make insecticidal compositions. They may be thus admixed with solid carriers, liquid carriers, gaseous carriers, food substances, etc. When necessary or desired, the mixtures may be further supplemented with surfactants and/or other adjuvants to make insecticidal compositions in forms such as oil sprays, emuisifiable concentrates, wettable powders, flowable concentrates (e.g. water-based suspension formulations, water-based emulsion formulations), granules, dusts, aerosols, heat smoking formulatins (e.g. self-burning type smoking formulations, chemical reaction type smoking formulations, porous ceramic plate type smoking formulations), ULV formulations, poison baits, etc.

The insecticidal composition of the invention comprises the carbamic acid derivative(s) (I) usually in a concentration of about 0.001 to 95% by weight.

Examples of the solid carrier used for making the insecticidal composition include fine pwoders or granules, etc. of clays (e.g. kaolin clay, diatomaceous earth, synthetic hydrated silicon dioxide, bentonite, Fubasami clay, terra alba, etc.), talc, ceramics, other inorganic minerals (e.g. sericite, quartz, sulfur, activated carbon, calcium carbonate, hydrated silica, etc.), chemical fertilizers (e.g. ammonium sulfate, ammonium phosphate, ammonium nitrate, urea, ammonium chloride, etc.), etc. Examples of the liquid carrier include water, alcohols (e.g. methanol, ethanol, etc.), ketones (e.g. acetone, methyl ethyl ketone, etc.), aromatic hydrocarbons (e.g. benzene, toluene, xylene, ethylbenzene, methylnaphthalene, etc.), aliphatic hydrocarbons (e.g. hexane, cyclohexane, kerosene, gas oil, etc.), esters (e.g. ethyl acetate, butyl acetate, etc.), nitriles (e.g. acetonitrile, isobutyronitrile, etc.), ethers (e.g. diisopropyl ether, dioaxane, etc.), acid amides (e.g. N,N-dimethylformamide, N,N-dimethylacetamide, etc.), halogehated hydrocarbons (e.g. dichloromethane, trichloroethane, carbon tetrachloride, etc.), dimethylsulfoxide, vegetable oils (e.g. soybean oil, cotton seed oil), etc. Examples of the gaseous carrier, i.e. propellant, inlcude freon gas, butane gas, LPG (liquefied petroleum gas), dimethyl ether, carbon dioxide, etc.

Examples of the surfactant include alkyl sulfates, alkyl sulfoates, alkylaryl sulfonates, alkyl aryl ethers and polyoxyethylene derivatives thereof, polyethylene glycol ether, polyvalent alcohol esters, sugar alcohol derivatives, tec.

Examples of the adjuvants such as binders, dispersing agents, etc. for formulations include casein, gelatin, polysaccharides (e.g. starch powders, gum arabic, cellulose derivatives, alginic acid, etc.), lignin derivatives, bentonite, sugars, synthetic water-soluble high molecular substances (e.g. polyvinyl alcohol, polyvinylpyrrolidone, polyacrylic acid, etc.). Examples of the stabilizer include PAP (acidic isopropyl phosphate), BHT (2,6-di-tert-butyl-4-methylphenol), BHA (mixture of 2-tert-butyl-4-methoxyphenol and 3-tert-butyl-4-methoxyphenol), vegetable oils, mineral oils, surfactants, fatty acids or esters thereof, and the like.

The base material for self-burning type smoking formulations includes, for example, heat-generating agents such as nitrates, nitrites, guanidine salts, potassium chlorate, nitrocellulose, ethyl cellulose, wood powders, etc.;

pyrolysis-promoting agents such as alkali metal salts, alkaline earth metal salts, dichromates, chromates, etc.; oxygen-supplying agnets such as potassium nitrate, etc.; burning-supporting agents such s melamine, wheat starch, etc.; extenders such as diatomaceous earth, etc.; and binders such as synthetic pastes, etc.

The base material for chemical reaction type smoking formulations includes, for example, heat-generating agents such as sulfides, polysulfides, hydrosulfides or salt hydrates of alkali metals, calcium oxide, etc.; catalyzing agents such as carbonaceous substances, iron carbide, activated clay, etc.; organic foaming agents such as azodicarbonamide, benzenesulfonyl hydrazide, dinitrosopentamethylenetetramine, polystyrene, polyurethane, etc.; fillers such as natural fiber pieces, synthetic fiber pieces, etc.

As the base material for poison baits, there are, for example, food components such as crop powders, essential vegetable oil, sugars, crystalline cellulose, etc.; antioxidants such as dibutylhydroxytoluene, nordihydroguaiaretic acid, etc.; preservatives such as dehydroacetic acid, etc.; mis-food preventing agents such as red pepper powders, etc.; incentive flavor such as cheese flavor, onion flavor, etc.

The flowable concentrates (water-based suspension formulatons or water-based emulsion formulations) are generally obtained by finely dispersing about 1 to 75% of the active ingredient into water containing about 0.5 to 15% of a dispersing agent, about 0.1 to 10% of a suspending agent such as protective colloids (e.g. gelatin, casein, gum arabic, cellulose ethers, polyvinyl alcohols, etc) and thixotropic property-giving compounds (e.g. bentonite, aluminum magnesium sulicate, xanthane gum, polyacrylic acid, etc.) and about 0 to 10% of other auxiliary agent(s) (e.g. defoaming agents, anticorrosives, stabilizers, spreading agents, penetration auxiliaries, antifreezing agents, antibacterial agents, antimolding agents). It is also possible to obtain oil-based suspension formulations by replacing water by an oil which hardly dissolves the active compound.

The thus obtained formulations may be used as they are or after diluting with water, etc. Alternatively, the formulations may be used as admixture with other insecticides, nematocides, acaricides, fungicides, bacteriocides, herbicides, plant growth controllers, synergistic agents, fertilizers, soil conditioners, animal food, etc., or may also be used simultaneously with them, without mixing therewith.

When the carbamic acid derivative (I) is used as the agent for controlling insect pests in agriculture, the dosage of the active ingredient may be generally from about 0.001 to 500 grams, preparably from about 0.1 to 500 grams, per 10 ares. In case of the composition being formulated into emulsifiable concentrates, wettable powders, flowable concentrates, etc., it is normally diluted with water and applied in a concentration of from about 0.0001 to 1,000 ppm. Granules, dusts, etc. may be used as such.

For the purpose of home and public hygiene, the composition in the form of emulsifiable concentrates, wettable powders or flowable concentrates, etc. is used as a dlution with water in a concentration of from about 0.0001 to 10,000 ppm. Oils, aerosols, fumigants, ULV formulations, poison baits, etc. can be used as such.

The above doses and concentrations may vary depending on kind of formulations, timing for application, place applied, method for application, kind and species of insects, condition of damages, etc. and may be icnreased or decreased, irrespective of the ranges set forth above.

The carbamic acid derivatives (I) may be employed in conjuction with other insecticides and/or acaricides to enhance their insecticidal and/or pesticidal activity. Examples of the other insecticides and/or acaricides include organophosphorus compounds (e.g. fenitrothion (O,O-dimethyl O-(3-methyl-4-nitrophenyl)phosphorothioate), fenthion (O,O-dimethyl O-[3-methyl-4-(methylthio)phenyl]phosphorothioate), diazinon (O,O-diethyl-O-(2-isopropyl-6-methylpyrimidin-4-yl)phosphorothioate), chlorpyrifos (O,O-di-ethyl-O-(3,5,6-trichloro-2-pyridyl)phosphorothioate), acephate (O,S-dimethyl acetylphosphoramidothioate), methidathion (S-2,3-dihydro-5-methoxy-2-oxo-1,3,4-thiadiazol-3-ylmethyl O,O-dimethylphosphorodithioate), disulfoton (O,O-diethyl S-2-ethylthioethyl phosphorothioate), DDVP (2,2-dichlorovinyldimethylphosphate), sulprofos (O-ethyl O-4-(methylthio)phenyl S-propyl phosphorodithioate), cyanophos (O-4-cyanophenyl O,O-dimethyl phosphorothioate), dioxabenzofos (2-methoxy-4H-1,3,2-benzodioxaphosphinine-2-sulphide), dimethoate (O,O-diethyl-S-(N-methylcarbamoylmethyl)dithiophosphate), phenthoate (ethyl 2-dimethoxyphosphinothioylthio(phenyl)acetate), malathion (diethyl (dimethoxyphosphinothioylthio)succinate), trichlorfon (dimethyl 2,2,2-trichloro-1-hydroxyethylphosphonate), azinphos-methyl (S-3,4-dihydro-4-oxo-1,2,3-benzotriazin-3-ylmethyl O,O-dimethylphosphoro-dithioate), monocrotophos (dimethyl (E)-1-methyl-2-(methylcarbamoyl)vinyl phosphate), etc.); carbamate derivatives (e.g. BPMC (2-sec-butylphenyl methylcarbamate), benfuracarb (ethyl N-[2,3-dihydro-2,2-dimethylbenzofuran-7-yloxycarbonyl(methyl)aminothio]-N-isopropyl-beta-alaninate), propoxur (2-isopropoxyphenyl N-methylcarbamate), carbosulfan (2,3-dihydro-2,2-dimethyl-7-benzo[b]furanyl N-methylcarbamate), carbaryl (1-naphthyl-N-methylcarbamate), methomyl (S-methyl-N-[(methylcarbamoyl)oxy]thioacetimidate), ethiofencarb (2-(ethylthiomethyl)phenyl methylcarbamate), aldicarb (2-methyl-2-(methylthio)propionaldehyde O-methylcarbamoyloxime), Oxamyl (N,N-dimethyl-2-methylcarbamoyloxyimino-2-(methylthio)acetamide), etc.); pyrethroides (e.g. ethofenprop (2-(4-ethoxyphenyl-2-methylpropyl-3-phenoxybenzylether), fenvalerate ((RS)-alpha-cyano-3-phenoxybenzyl (RS)-2-(4-chlorophenyl)-3-methylbutyrate), esfenvalerate ((S)-alpha-cyano-3-phenoxybenzyl (S)-2-(4-chlorophenyl)-3-methylbutyrate), fenpropathrin ((RS)-alpha-cyano-3-phenoxybenzyl 2,2,3,3-tetramethylcyclopropanecarboxylate), cypermethrin ((RS)-alpha-cyano-3-phenoxybenzyl (1RS,3RS)-(1RS,3RS)-3-(2,2-dichlorovinyl)-2,2-dimethylcyclopropanecarboxylate), permethrin (3-phenoxybenzyl (1RS,3RS)-(1RS,3RS)-3-(2,2-dichlorovinyl)-2,2-dimethylcyclopropanecarboxylate), cyhalothrin ((R,S)-alpha-cyano-3-phenoxybenzyl (Z)-(1RS,3RS)-3-(2-chloro-3,3,3-trifluoropropenyl)-2,2-dimethylcyclopropanecarboxylate), deltamethrin ((S)-alphacyano-m-phenoxybenzyl (1R,3R)-3-(2,2-dibromovinyl)-2,2-dimethylcyclopropanecarboxylate), cycloprothrin ((RS)-alphacyano-3-phenoxybenzyl (RS)-2,2-dichloro-1-(4-ethoxyphenyl)cyclopropanecarboxylate), etc.); thiadiazine derivatives (e.g. buprofezin (2-tert-butylimino-3-isopropyl-5-phenyl-1,3,5-triazin-4-one), etc.); nitroimidazolidine derivatives (e.g. imidacloprid (1-((6-chloro-3-pyridylmethyl)-N-nitroimidazolidin-2-ylideneamine), etc.); nereistoxin derivatives (e.g. cartap (S,S'-(2-dimethylaminotrimethylene) bis(thiocarbamate), thiocyclam (N,N-dimethyl-1,2,3-trithian-5-ylamine), bensultap (S,S'-2-dimethylaminotrimethylene di(benzenethiosulphonate), etc.); halogenated hydrocarbons (e.g. endosulfan (6,7,8,9,10,10-hexachloro-1,5,5a,6,9,9a-hexahydro-6,9-methano-2,4,3-benzodioxathiepin-3-oxide), gamma-BHC (1,2,3,4,5,6-hexachlorocyclohexane), etc.); benzoylphenylurea derivatives (e.g. chlorfluazuron (1-[3,5-dichloro-4-(3-chloro-5-trifluoromethylpyridin-2-yloxy)phenyl]-3-(2,6-difluorobenzoyl)urea), teflubenzuron (1-(3,5-dichloro-2,4-difluorophenyl)-3- (2,6-difluorobenzoyl)urea), flufenoxuron (1-[4-(2-chloro-4-trifluoromethylphenoxy)-2-fluorophenyl]-3-(2,6-difluorobenzoyl)urea, etc.); formamidine derivatives (e.g. amitraz (N,N'-[(methylimino)di-methylidyne] di-2,4-xylidine), chlordimeform (N'-(4-chloro-2-methylphenyl)-N,N-dimethylmethanimidamide), etc.).

EXAMPLES

Practical and presently preferred embodiments of the present invention will be explained in more detail with reference to production examples, formulation examples and test examples. However, these examples shall not be deedmed to make limitation onto the scope of this invention in any way.

PRODUCTION EXAMPLE 1

Production of Compound (1) by Process (A)

To a solution of 0.52 g of 2-(2-chloro-4-phonoxyphenoxy)ethylamine and 1.12 g of ethyl chloroformate in 20 ml of acetone, there were added 1.66 g of potassium carbonate, and the resultant mixture was refluxed under heating and stirring for 24 hours. The reaction mixture was concentrated and poured into 50 ml of water, followed by extraction twice with 100 ml of ethyl acetate. The extracts were combined together, dried over anhydrous magnesium sulfate and concentrated under reduced pressure. The residue was was subjected to silica gel chromatography to give 0.39 g of ethyl 2-[2-chloro-4-phenoxyphenoxy]ethylcarbamate. Yield: 59%. $n_D^{24}$: 1.5632.

PRODUCTION EXAMPLE 2

Production of Compound (6) by Process (B)

To a solution of 0.89 g o#2-(2-chloro-4-phenoxyphenoxy)ethylisocyanide in 10 ml of methanol, there were added a few drops of pyridine, and the resultant mixture was refluxed under heating for one hour. The reaction mixture was concentrated under reduced pressure. The residue was subjected to silica gel chromatography to give 0.51 g of methyl 2-[2-chloro-4-phenoxyphenoxy]ethylcarbamate. Yield: 52%. $n_D^{23}$: 1.5698.

PRODUCTION EXAMPLE 3

Production of Compound (8) by Process (C)

To a solution of 0.91 g of 2-chloro-5-phenoxyphenol in 20 ml of N,N-dimethylformamide, there were added 0.69 g of ethyl 2-chloroethylcarbamate and 1.14 g of potassium carbonate with stirring, and the resultant mixture was stirred at 50° C. for 7 hours. The reaction mixture was poured into 100 g of ice-water and extracted twice with 100 ml of ethyl acetate. The extracts were combined together, dried over anhydrous magnesium sulfate and concentrated under reduced pressure. The residue was subjected to silica gel chromatography to give 0.14 g of ethyl 2-(2-chloro-5-phenoxyphenoxy)ethylcarbamate. Yield: 10%. $n_D^{22}$: 1.5608.

PRODUCTION EXAMPLE 4

Production of Compound (100) by Process (C)

To a solution of 0.5 g (1.73 mmol) of 2-chloro-4-(3-trifluoromethylphenoxy)phenol in 20 ml of N,N-dimethylfomamide, there are added 0.29 g (1.90 mmol) of ethyl 2-chloroethylcarbamate and 0.53 g (3.81 mmol) of potassium carbonate with stirring, and the resultant mixture is heated at 50° C. for 7 hours. The reaction mixture is poured into 100 g of ice-water and extracted twice with 100 ml of ethyl acetate. The extracts are combined together, dried over anhydrous magnesium sulfate and concentrated under reduced pressure. The residue is subjected to silica gel chromatography to give ethyl 2-[2-chloro-4-(3-trifluoromethylphenoxy)phenoxy]ethylcarbamate.

PRODUCITON EXAMPLE 5

Produciton of Compound (116) by Process (C)

To a solution of 0.65 g (2.25 mmol) of 2-chloro-4-(4-trifluoromethylphenoxy)-phenol in 20 ml of N,N-dimethylformamide, there are added 0.38 g (2.47 mmol) of ethyl 2-chloroethylcarbamate and 0.69 g (4.95 mmol) of potassium carbonate with stirring, and the resultant mixture is stirred at 50° C. for 8 hours. The reaction mixture is poured into 100 g of ice-water and extracted twice with 100 ml of ethyl acetate. The extracts are combined together, dried over anhydrous magnesium sulfate and concentrated under reduced pressure. The residue is subjected to silica gel chromatography to give ethyl 2-[2-chloro-4-(4-trifluoromethylphenoxy)phenoxy]ethylcarbamate.

PRODUCTION EXAMPLE 6

Production of Compound (15) by Process (D)

Into a mixture of 1.20 g of 2-[2-chloro-4-(3,5difluorophenoxy)phenoxy]ethylamine, 0.81 g of triethylamine and 20 ml of tetrahydrofuran, excesss of carbonyl sulfide gas was introduced with stirring at room temperature for 30 minutes. To the above mixture, there was added dropwise 0.75 g of ethyl iodide, and the resultant mixture was stirred at the same temperature for 24 hours. The reaction mixture was concentrated, and the residue was poured into 100 ml of water and extracted twice with 100 ml of ethyl acetate. The extracts were combined together, dried over anhydrous magnesium sulfate and concentrated under reduced pressure. The residue was subjected to silica gel chromatography to give 0.95 g of ethyl 2-[2-chloro-4-(3,5-difluorophenoxy)phenoxy]ethylthiocarbamate. Yield: 61%. $n_D^{21}$: 1.5707.

PRODUCTION EXAMPLE 7

Production of Compound (153) by Process (E)

A mixture of 0.85 g (2.29 mmol) of ethyl 2-[2-chloro-4-(3,5-difluorophenoxy)phenoxy]ethylcarbamate in 10 ml of methylene chloride is cooled at 0° C., and 0.26 g (2.52 mmol) of triethylamine is added thereto with stirring, followed by cooling at 0° to 5° C. To the resulting mixture, a solution of 0.36 g of methyl N-chlorosulfenyl-N-methylcarbamate in 3 ml of methylene chloride is dropwise added, followed by stirring at room temperature for 1 hour. The reaction mixture is poured into water and extracted twice with 500 ml of diethyl ether.

The extracts are combined together, dried over anhydrous magnesium sulfate and concentrated under reduced pressure. The residue is subjected to silica gel chromatography to give ethyl [N-(methoxycarbonylmethylamino)sulfenyl]-2-[4-(3,5-difluorophenoxy)-phenoxy]ethylcarbamate.

In the same manner as above, the carbamic acid derivatives (I) as shown below are obtained.

(1) Ethyl 2-(2-chloro-4-phenoxyphenoxy)ethylcarbamate. $n_D^{24}$: 1.5632.
(2) n-Pentyl 2-(2-chloro-4-phenoxyphenoxy)ethylcarbamate. $n_D^{22}$: 1.5489.
(3) Allyl 2-(2-chloro-4-phenoxyphenoxy)ethylcarbamate. $n_D^{22}$: 1.5671.
(4) 2-Methoxyethyl 2-(2-chloro-4-phenoxyphenoxy)ethylcarbamate. $n_D^{22}$: 1.5583.
(5) 2-Trichloroethyl 2- (2-chloro-4-phenoxyphenoxy)ethylcarbamate. $n_D^{22}$: 1.5650.
(6) Methyl 2- (2-chloro-4-phenoxyphenoxy)ethylcarbamate. $n_D^{23}$: 1.5698.
(7) n-Propyl 2- (2-chloro-4-phenoxyphenoxy)ethylcarbamate. viscous liquid.
(8) Isopropyl 2- (2-chloro-4-phenoxyphenoxy)ethylcarbamate. $n_D^{24}$: 1.5542.
(9) n-Butyl 2- (2-chloro-4-phenoxyphenoxy)ethylcarbamate. $n_D^{22}$: 1.5530.
(10) Isobutyl 2- (2-chloro-4-phenoxyphenoxy)ethylcarbamate. $n_D^{22}$: 1.5505.
(11) Ethyl 2-[2-chloro-4-(3,5-difluorophenoxy)phenoxy]ethylcarbamate. $n_D^{22}$: 1.5420.
(12) Ethyl 2-[2-chloro-4-(3-fluorophenoxy)phenoxy]ethylcarbamate. $n_D^{22}$: 1.5498.
(13) Ethyl 2-[2-chloro-4-(3-methylphenoxy)phenoxy]ethylcarbamate. $n_D^{20}$: 1.5627.
(14) Ethyl 2-[2-chloro-4-(2,4-difluorophenoxy)phenoxy]ethylcarbamate. $n_D^{25}$: 1.5089.
(15) Ethyl 2-[2-chloro-4-(3,5-difluorophenoxy)phenoxy]ethylthiocarbamate. $n_D^{21}$: 1.5707.
(16) Ethyl 2-(2-chloro-4-benzylphenoxy)ethylcarbamate. $n_D^{20}$: 1.5648.
(17) Ethyl 2-(2-chloro-4-benzoylphenoxy)ethylcarbamate. viscous liquid.
(18) Ethyl 2-(2-chloro-5-phenoxyphenoxy)ethylcarbamate. $n_D^{22}$: 1.5608.
(19) Ethyl 2-(2-chloro-4-phenoxyphenoxy)ethylthiocarbamate. $n_D^{20.8}$: 1.5927.
(20) Ethyl 2-[2,6-dichloro-4-(3,5-difluorophenoxy)phenoxy]ethylcarbamate. $n_D^{25}$: 1.5361.
(21) Ethyl 2-[2-chloro-4-(3,4-dichlorobenzyl)phenoxy]ethylcarbamate. $n_D^{22.8}$: 1.5682.
(22) Ethyl 2-[2-chloro-4-(3,5-difluorobenzyl)phenoxy]ethylcarbamate. $n_D^{26.2}$: 1.5422.
(23) Ethyl 2-[2-chloro-5-(3,5-difluorophenoxy)phenoxy]ethylcarbamate. $n_D^{23.3}$: 1.5329.
(24) Ethyl 2-[2-chloro-5-(3,4-dichlorophenoxy)phenoxy]ethylcarbamate. $n_D^{24}$: 1.5751.
(25) Ethyl 2-[2,5-dichloro-4-(3,5-difluorophenoxy)phenoxy]ethylcarbamate. $n_D^{25}$: 1.5421.
(26) Ethyl 2-[2-chloro-4-(3,4-dichlorophenoxy)phenoxy]ethylcarbamate. $n_D^{26}$: 1.5709.
(27) 2,2,2-Trichloroethyl 2-[2-chloro-4-(3,5-difluorophenoxy)phenoxy]ethylcarbamate. $n_D^{23.5}$: 1.5450.
(28) 2-Chloroethyl 2-[2-chloro-4-(3,5-difluorophenoxy)phenoxy]ethylcarbamate. $n_D^{23.6}$: 1.5515.
(29) 2,2,2-Trifluoroethyl 2-[2-chloro-4-(3,5-difluorophenoxy)phenoxy]ethylcarbamate. $n_D^{23.7}$: 1.5110.
(30) 2-Chloroethyl 2-(2-chloro-4-benzylphenoxy)ethylcarbamate. $n_D^{22.6}$: 1.5708.
(31) 2,2-Dichloroethyl 2-(2-chloro-4-benzylphenoxy)ethylcarbamate. $n_D^{22.6}$: 1.5740.
(32) 2,2,2-Trifluoroethyl 2-(2-chloro-4-benzylphenoxy)ethylcarbamate. $n_D^{22.4}$: 1.5369.
(33) 2,2,2-Trichloroethyl 2-(2-chloro-4-benzylphenoxy)ethylcarbamate. $n_D^{20.4}$: 1.5728.
(34) 2-Bromoethyl 2-(2-chloro-4-benzylphenoxy)ethylcarbamate. $n_D^{22.5}$: 1.5802.
(35) 2,2,2-Tribromoethyl 2-(2-chloro-4-benzylphenoxy)ethylcarbamate. m.p. 64.3° C.
(36) 2,2,3,3,4,4,4-Heptafluoro-n-butyl 2-(2-chloro-4-benzylphenoxy)ethylcarbamate. $n_D^{20.5}$: 1.4991.
(37) 2-Iodoethyl 2-(2-chloro-4-benzylphenoxy)ethylcarbamate. $n_D^{22}$: 1.5897.
(38) 3-Bromo-n-propyl 2-(2-chloro-4-benzylphenoxy)ethylcarbamate. $n_D^{21.3}$: 1.5766.
(39) 2-Chloroethyl 2-[2-chloro-4-(3-chlorophenoxy)phenoxy]ethylcarbamate. $n_D^{23}$: 1.5590.
(40) 2,2-Dichloroethyl 2-[2-chloro-4-(3-chlorophenoxy)phenoxy]ethylcarbamate. $n_D^{23}$: 1.5646.
(41) 2,2,2-Trichloroethyl 2-[2-chloro-4-(3-chlorophenoxy)phenoxy]ethylcarbamate. $n_D^{23}$: 1.5562.
(42) 2,2,2-Trifluoroethyl 2-[2-chloro-4-(3-chlorophenoxy)phenoxy]ethylcarbamate. $n_D^{23}$: 1.5302.
(43) 3-Chloro-n-propyl 2-[2-chloro-4-(3-chlorophenoxy)phenoxy]ethylcarbamate. $n_D^{23}$: 1.5581,
(44) 1-Chloromethyl-2-chloroethyl 2-[2-chloro-4-(3-chlorophenoxy)phenoxy]ethylcarbamate. $n_D^{23}$: 1.5505.
(45) 1,2-Dichloroethyl 2-[2-chloro-4-(3-chlorophenoxy)phenoxy]ethylcarbamate. $n_D^{23}$: 1.5660.
(46) 2-Chloro-1-methylethyl 2-[2-chloro-4-(3-chlorophenoxy)phenoxy]ethylcarbamate. $n_D^{23}$: 1.5642.
(47) 2-Ethoxyethyl 2-[2-chloro-4-(3-chlorophenoxy)phenoxy]ethylcarbamate. $n_D^{23}$: 1.5522.
(48) 1-Trifluoromethyl-2,2,2-trifluoroethyl 2-[2-chloro-4-(3-chlorophenoxy)phenoxy]ethylcarbamate. m.p. 84.5° C.
(49) Ethyl 1-methyl-2-[2-chloro-4-(3,5-difluorophenoxy)phenoxy]ethylcarbamate.
(50) 2-Fluoroethyl 2-(2-chloro-4-benzylphenoxy)ethylcarbamate. $n_D^{20.6}$: 1.5598.
(51) 3-Chloro-n-propyl 2-(2-chloro-4-benzylphenoxy)ethylcarbamate. $n_D^{20.9}$: 1.5682.
(52) 2-Bromo-1-methylethyl 2-(2-chloro-4-benzylphenoxy)ethylcarbamate. $n_D^{21.2}$: 1.5721.
(53) 2-Chloro-1-methylethyl 2-(2-chloro-4-benzylphenoxy)ethylcarbamate. $n_D^{26.0}$: 1.5630.
(54) 2,2,3,3-Tetrafluoro-n-propyl 2-(2-chloro-4-benzylphenoxy)ethylcarbamate. $n_D^{24.9}$: 1.5256.
(55) 2-Cyanoethyl 2-(2-chloro-4-benzylphenoxy)ethylcarbamate. $n_D^{20.7}$: 1.5672.
(56) 2,2,3,3,3-Pentafluoro-n-propyl 2-(2-chloro-4-benzylphenoxy)ethylcarbamate. $n_D^{20.8}$: 1.5118.
(57) 2-Propynyl 2-(2-chloro-4-benzylphenoxy)ethylcarbamate. m.p. 70.4° C.
(58) 1-Trifluoromethylethyl 2-(2-chloro-4-benzylphenoxy)ethylcarbamate. $n_D^{21.2}$: 1.5342.
(59) 1-Methyl-2-propynyl 2- (2-chloro-4-benzylphenoxy)ethylcarbamate. $n_D^{21.3}$: 1.5637.
(60) 2,3-Dichloro-n-propyl 2-(2-chloro-4-benzylphenoxy)ethylcarbamate. $n_D^{24}$: 1.5460.
(61) Isopropyl 2-(2-chloro-4-benzylphenoxy)ethylcarbamate. $n_D^{20.7}$: 1.5580.
(62) 1-Trifluoromethyl-2,2,2-trifluoroethyl 2-(2-chloro-4-benzylphenoxy)ethylcarbamate. m.p. 89.5° C.
(63) 2-Methoxyethyl 2-(2-chloro-4-benzylphenoxy)ethylcarbamate. $n_D^{22.4}$:1.5562.

(64) 2-Fluoroethyl 2-[2-chloro-4-(3-chlorophenoxy)-phenoxy]ethylcarbamate. $n_D^{23}$: 1.5684.

(65) Tert-butyl 2-(2-chloro-4-benzylphenoxy)ethylcarbamate. $n_D^{22.1}$: 1.5569.

(66) 1,1-Dimethyl-2-propynyl 2-(2-chloro-4-benzylphenoxy)ethylcarbamate. $n_D^{22.6}$: 1.5605.

(67) 1,1-Dimethyl-2-propenyl 2-(2-chloro-4-benzylphenoxy)ethylcarbamate. $n2D^{21.9}$: 1.5728.

(68) Isopropyl 2-[2-chloro-4-(3-chlorophenoxy)phenoxy]ethylcarbamate. $n_D^{20.5}$: 1.5570.

(69) 2-Methoxyethyl 2-[2-chloro-4-(3-chlorophenoxy)-phenoxy]ethylcarbamate. $n_D^{20.5}$: 1.5586.

(70) 2-cyanoethyl 2-[2-chloro-4-(3-chlorophenoxy)-phenoxy]ethylcarbamate. $n_D^{23}$: 1.5604.

(71) 2-Bromoethyl 2-[2-chloro-4-(3-chlorophenoxy)-phenoxy]ethylcarbamate. $n_D^{23}$: 1.5797.

(72) 2,2,2-Tribromoethyl 2-[2-chloro-4-(3-chlorophenoxy)phenoxy]ethylcarbamate. $n_D^{23}$: 1.6002.

(73) 2-Bromo-1-methylethyl 2-[2-chloro-4-(3-chlorophenoxy)phenoxy]ethylcarbamate. $n_D^{23}$: 1.5688.

(74) 1-Fluoromethyl-2-fluoroethyl 2-[2-chloro-4-(3-chlorophenoxy)phenoxy]ethylcarbamate. $n_D^{23}$: 1.5553.

(75) 2,3-Dibromo-n-propyl 2-[2-chloro-4-(3-chlorophenoxy)phenoxy]ethylcarbamate. $n_D^{23}$: 1.5902.

(76) 2,2,3,3-Tetrafluolo-n-propyl 2-[2-chloro-4-(3-chlorophenoxy)phenoxy]ethylcarbamate. $n_D^{23}$: 1.5322.

(77) 1-Trifluoromethylethyl 2-[2-chloro-4-(3chlorophenoxy)phenoxy]ethylcarbamate. $n_D^{23}$: 1.5368.

(78) 2,2,3,3,3-Pentafluoro-n-propyl 2-[2-chloro-4-(3-chlorophenoxy)phenoxy]ethylcarbamate. $n_D^{23}$: 1.5149.

(79) 2-Propynyl 2-[2-chloro-4-(3-chlorophenoxy)-phenoxy]ethylcarbamate. $n_D^{24}$: 1.5690.

(80) 2-Butenyl 2-[2-chloro-4-(3-chlorophenoxy)phenoxy]ethylcarbamate. $n_D^{24}$: 1.5685.

(81) 2-Methylpropyl 2-[2-chloro-4-(3-chlorophenoxy)-phenoxy]ethylcarbamate. $n_D^{24}$: 1.5547.

(82) 3-Butynyl 2-[2-chloro-4-(3-chlorophenoxy)phenoxy]ethylcarbamate. $n_D^{24}$: 1.5591.

(83) 2-Butynyl 2-[2-chloro-4-(3-chlorophenoxy)phenoxy]ethylcarbamate. $n_D^{24}$: 1.5636.

(84) 2,2,3,3,4,4,4-Heptafluoro-n-butyl 2-[2-chloro-4-(3-chlorophenoxy)phenoxy]ethylcarbamate. $n_D^{24}$: 1.5003.

(85) Ethyl 2-[2-chloro-4-(3-bromophenoxy)phenoxy]ethylcarbamate.

(86) 1-Fluoromethyl-2-fluoroethyl 2-(2-chloro-4-benzylphenoxy)ethylcarbamate. $n_D^{21.4}$: 1.5460.

(87) 2,3-Dibromo-n-propyl 2-(2-chloro-4-benzylphenoxy)ethylcarbamate. $n_D^{21.8}$: 1.5800.

(88) 2-Ethoxyethyl 2-(2-chloro-4-benzylphenoxy)ethylcarbamate. $n_D^{21.2}$: 1.5541.

(89) 1-Chloromethyl-2-chloroethyl 2-(2-chloro-4-benzylphenoxy)ethylcarbamate. $n_D^{21.3}$: 1.5680.

(90) 2-Butenyl 2-(2-chloro-4-benzylphenoxy)ethylcarbamate. $n_D^{21.3}$: 1.5656.

(91) Isobutyl 2-(2-chloro-4-benzylphenoxy)ethylcarbamate. $n_D^{21.5}$: 1.5539.

(92) 2-Butynyl 2-(2-chloro-4-benzylphenoxy)ethylcarbamate. $n_D^{21.8}$: 1.5728.

(93) 3-Butynyl 2-(2-chloro-4-benzylphenoxy)ethylcarbamate. $n_D^{21.6}$: 1.5691.

(94) 3-Butenyl 2-(2-chloro-4-benzylphenoxy)ethylcarbamate. $n_D^{20}$: 1.5650.

(95) 4,4,4-Trifluoro-n-butyl 2-(2-chloro-4-benzylphenoxy)ethylcarbamate. $n_D^{20}$: 1.5311.

(96) 1-Methyl-n-propyl 2-(2-chloro-4-benzylphenoxy)ethylcarbamate. $n_D^{20.6}$: 1.5542.

(97) 1-Methoxyethyl 2-(2-chloro-4-benzylphenoxy)ethylcarbamate. $n_D^{20.1}$: 1.5550.

(98) 2-Methyl-3-butenyl 2-(2-chloro-4-benzylphenoxy)ethylcarbamate. $n_D^{20.3}$: 1.5661.

(99) 2-Isopropoxyethyl 2-(2-chloro-4-benzylphenoxy)ethylcarbamate. $n_D^{20.8}$: 1.5478.

(100) Ethyl 2-[2-chloro-4-(3-trifluoromethylphenoxy)-phenoxy]ethylcarbamate.

(101) 3-Methyl-2-butenyl 2-(2-chloro-4-benzylphenoxy)ethylcarbamate. $n_D^{20}$: 1.5582.

(102) 2,2-Dimethyl-n-propyl 2-(2-chloro-4-benzylphenoxy)ethylcarbamate. $n_D^{19.9}$: 1.5481.

(103) 3,3-Dimethyl-n-butyl 2-(2-chloro-4-benzylphenoxy)ethylcarbamate. $n_D^{20.4}$: 1.5469.

(104) 3-Methyl-n-butyl 2-(2-chloro-4-benzylphenoxy)ethylcarbamate. $n_D^{20.3}$: 1.5495.

(105) 2-Methylthioethyl 2-(2-chloro-4-benzylphenoxy)ethylcarbamate. $n_D^{20.6}$: 1.5797.

(106) Ethyl 2-(2-fluoro-4-phenoxyphenoxy)ethylcarbamate. $n_D^{24.0}$: 1.5338.

(107) 2-Bromo-1-methylethyl 2-[2-chloro-4-(3,5-difluorophenoxy)phenoxy]ethylcarbamate. $n_D^{21}$: 1.5506.

(108) Tert-butyl 2-[2-chloro-4-(3-chlorophenoxy)-phenoxy]ethylcarbamate. $n_D^{22}$: 1.5320.

(109) 3-Butenyl 2-[2-chloro-4-(3-chlorophenoxy)-phenoxy]ethylcarbamate. $n_D^{22}$: 1.5519.

(110) 1-Methyl-n-propyl 2-[2-chloro-4-(3-chlorophenoxy)phenoxy]ethylcarbamate. $n_D^{21.5}$: 1.5582.

(111) 2-Methoxy-1-methylethyl 2-[2-chloro-4-(3-chlorophenoxy)phenoxy]ethylcarbamate. $n_D^{21.5}$: 1.5614.

(112) 1-Methyl-2-propenyl 2-[2-chloro-4-(3-chlorophenoxy)phenoxy]ethylcarbamate. $n_D^{21.5}$: 1.5573.

(113) 1-Methyl-2-propynyl 2-[2-chloro-4-(3-chlorophenoxy)phenoxy]ethylcarbamate. $n_D^{21.5}$: 1.5519.

(114) 1,1-Dimethyl-2-propynyl 2-[2-chloro-4-(3chlorophenoxy)phenoxy]ethylcarbamate. $n_D^{23}$: 1.5299.

(115) 2-Isopropoxyethyl 2-[2-chloro-4-(3-chlorophenoxy)phenoxy]ethylcarbamate. $n_D^{22.5}$ 1.5510.

(116) Ethyl 2-[2-chloro-4-(4-trifluoromethylphenoxy)-phenoxy]ethylcarbamate.

(117) 1,1-Dimethyl-2-propenyl 2-[2-chloro-4-(3chlorophenoxy)phenoxy]ethylcarbamate. $n_D^{23}$: 1.5491.

(118) 3-Methyl-2-butenyl 2-[2-chloro-4-(3-chlorophenoxy)phenoxy]ethylcarbamate. $n_D^{22.5}$: 1.5648.

(119) 2,2-Dimethyl-n-propyl 2-[2-chloro-4-(3-chlorophenoxy)phenoxy]ethylcarbamate. $n_D^{22.5}$: 1.5543.

(120) 3,3-Dimethyl-n-butyl 2-[2-chloro-4-(3-chlorophenoxy)phenoxy]ethylcarbamate. $n_D^{22.5}$: 1.5693.

(121) 3-Methyl-n-butyl 2-[2-chloro-4-(3-chlorophenoxy)phenoxy]ethylcarbamate. $n_D^{22.5}$: 1.5591.

(122) 2-Iodoethyl 2-[2-chloro-4-(3-chlorophenoxy)-phenoxy]ethylcarbamate. $n_D^{22.5}$: 1.5624.

(123) 2-Methylthioethyl 2-[2-chloro-4-(3-chlorophenoxy)phenoxy]ethylcarbamate. $n_D^{22.5}$: 1.5631.

(124) Ethyl 2-[2-chloro-4-(4-fluorophenoxy)phenoxy]ethylcarbamate. $n_D^{24}$: 1.5392.

(125) Ethyl 2-[2-chloro-4-(4-chlorophenoxy)phenoxy]ethylcarbamate. $n_D^{24}$: 1.5528.

(126) 1-Fluoromethyl-2-fluoroethyl 2-[2-chloro-4-(3,5-difluorophenoxy)phenoxy]ethylcarbamate. $n_D^{22.1}$: 1.5284.

(127) Methyl 2-[2-chloro-4-(3,5-difluorophenoxy)-phenoxy]ethylcarbamate. $n_D^{23.5}$: 1.5409.

(128) 2,3-Dibromo-n-propyl 2-[2-chloro-4-(3,5-difluorophenoxy)phenoxy]ethylcarbamate. $n_D^{22.8}$: 1.5634.
(129) Ethoxyethyl 2-[2-chloro-4-(3,5-diflurorophenoxy)phenoxy]ethylcarbamate. $n_D^{23.7}$: 1.5340.
(130) 1-Trifluoromethyl-2,2,2-trifluoroethyl 2-[2-chloro-4-(3,5-difluorophenoxy)phenoxy]ethylcarbamate. m.p. 78.1° C.
(131) 2,2,3,3-Tetrafluoro-n-propyl 2-[2-chloro-4-(3,5-difluorophenoxy)phenoxy]ethylcarbamate. $n_D^{22.9}$: 1.5045.
(132) 1-Trifluoromethylethyl 2-[2-chloro-4-(3,5-difluorophenoxy)phenoxy]ethylcarbamate. $n_D^{23.2}$: 1.5090.
(133) 2,2,3,3,3-Pentafluoro-n-propyl 2-[2-chloro-4-(3,5-difluorophenoxy)phenoxy]ethylcarbamate. $n_D^{23.2}$: 1.4938.
(134) 2-Propynyl 2-[2-chloro-4-(3,5-difluorophenoxy)phenoxy]ethylcarbamate. $n_D^{23.2}$: 1.5462.
(135) 2-Butenyl 2-[2-chloro-4-(3,5-difluorophenoxy)phenoxy]ethylcarbamate. $n_D^{23.2}$: 1.5409.
(136) Methyl 2-[2-chloro-4-benzylphenoxy]ethylcarbamate. $n_D^{18.7}$: 1.5748.
(137) 2-Methyl-n-propyl 2-(2-chloro-4-(3,5-difluorophenoxy)phenoxy]ethylcarbamate. $n_D^{24.5}$: 1.5304.
(138) 3-Butynyl 2-[2-chloro-4-(3,5-difluorophenoxy)phenoxy]ethylcarbamate. $n_D^{24.1}$: 1.5449.
(139) 2-Butynyl 2-[2-chloro-4-(3,5-difluorophenoxy)phenoxy]ethylcarbamate. $n_D^{23.6}$: 1.5475.
(140) 2,2,3,3,4,4,4-Heptafluoro-n-butyl 2-[2-chloro-4-(3,5-difluorophenoxy) phenoxy]ethylcarbamate. $n_D^{23.6}$: 1.4832.
(141) 3-Butenyl 2-[2-chloro-4-(3,5-difluorophenoxy)phenoxy]ethylcarbamate. $n_D^{24.2}$: 1.5408.
(142) 4,4,4-Trifluoro-n-butyl 2-[2-chloro-4-(3,5-difluorophenoxy)phenoxy]ethylcarbamate. $n_D^{23.7}$: 1.5080.
(143) 1-Methyl-n-propyl 2-[2-chloro-4-(3,5-difluorophenoxy)phenoxy]ethylcarbamate. m.p. 58.2° C.
(144) 1-Methoxyethyl 2-[2-chloro-4-( 3,5-difluorophenoxy)phenoxy]ethylcarbamate. $n_D^{23.5}$: 1.5298.
(145) Ethyl 2- [2-chloro-4-(3-chlorophenoxy)phenoxy]ethylcarbamate. $n_D^{26}$: 1.5611.
(146) 3-Chloropropyl 2-[2-chloro-4-(3,5-difluorophenoxy)phenoxy]ethylcarbamate. $n_D^{21.2}$: 1.5452.
(147) Ethyl 2-(2-bromo-4-phenoxyphenoxy)ethylcarbamate. $n_D^{24.0}$: 1.5798.
(148) Ethyl 2-(2-methyl-4-phenoxyphenoxy)ethylcarbamate. $n_D^{24}$: 1.5568.
(149) 4,4,4-Trifluoro-n-butyl 2-[2-chloro-4-(3-chlorophenoxy)phenoxy]ethylcarbamate. $n_D^{24}$: 1.5197.
(150) Cyclopentyl 2-(2-chloro-4-benzylphenoxy)ethylcarbamate. $n_D^{20.9}$: 1.5691.
(151) Cyclopentyl 2-[2-chloro-4-(3-chlorophenoxy)phenoxy]ethylcarbamate. $n_D^{22.5}$: 1.5632.
(152) 2,2-Dichloroethyl 2-[2-chloro-4-(3,5-difluorophenoxy)phenoxy]ethylcarbamate. $n_D^{20.6}$: 1.5502.
(153) Ethyl [N-(methoxycarbonylmethylamino)sulfenyl]-2-[4-(3,5-difluorophenoxy)phenoxy]ethylcarbamate.
(154) Methyl 2-[2-chloro-4-(3-chlorophenoxy)phenoxy]ethylcarbamate. $n_D^{26.9}$: 1.5740.

Some examples for production of intermediary compounds are shown below.

PRODUCTION EXAMPLE 8

Production of Compound (204)

A mixture of 14.99 g of 2-chloro-4-(3-chlorophenoxy)phenol, 4.44 g of chloroacetonitrile and 8.94 g of potassium carbonate in 150 ml of dimethylformamide was stirred at a temperature of 70° to 80° C. in an oil bath for 5 hours. The reaction mixture was cooled to room temperature, poured into water and extracted twice with 100 ml of ethyl acetate. The extracts were combined together, washed twice with 200 ml of water, dried over anhydrous magnesium sulfate and concentrated under reduced pressure to give 14.0 g of [2-chloro-4-(3-chlorophenoxy)phenoxy]acetonitrile as a crude product.

A solution of 14.0 g of the crude product as above obtained in 200 ml of tetrahydrofuran was kept at 0° C., and 200 ml of borane tetrahydrofuran complex (1.0M tetrahydrofuran solution) were dropwise added thereto with stirring at a temperature of 0° to 5° C. The resultant mixure was stirred at room temperature overnight and then poured into 300 ml of water, followed by removal of tetrahydrofuran by distillation under reduced pressure. The reaction-product was salted out and extracted three times with 100 ml of ethyl acetate. The extracts were combined together, washed with 0 ml each of a 5% aqueous solution of hydrochloric acid, water and a 10% aqueous solution of sodium hydroxide, dried over anhydrous magnesium sulfate and concentrated under reduced pressure-to give 11.4 g of 2-[2-chloro-4-(3-chlorophenoxy)phenoxy]ethylamine. Yield: 65%. $n_D^{24.3}$: 1.5842.

In the same manner as above, the following compounds are obtained.
(201) 2-(2-Chloro-4-phenoxyphenoxy)ethylamine. $n_D^{24.3}$: 1.5911.
(202) 2-(2-Chloro-4-benzylphenoxy)ethylamine. $n_D^{24.3}$: 1.5851.
(203) 2-[2-Chloro-4-(3,5-difluorophenoxy)phenoxy]ethylamine. $n_D^{24.3}$: 1.5620.
(204) 2-[2-Chloro-4-(3-chlorophenoxy)phenoxy]ethylamine. $n_D^{24.3}$: 1.5842.
(205) 2-[2-Chloro-4-(3-fluorophenoxy)phenoxy]ethylamine. $n_D^{24.3}$: 1.5769.
(206) 2-[2-Chloro-4-(3-methylphenoxy)phenoxy]ethylamine. $n_D^{24.3}$: 1.5842.
(207) 2-[2-Chloro-4-(3-trifluoromethoxyphenoxy)phenoxy]ethylamine.
(208) 2-[2-Chloro-4-(2,4-difluorophenoxy)phenoxy]ethylamine. $n_D^{24.3}$: 1.5599.
(209) 2-(2-Chloro-4-benzoylphenoxy)ethylamine. $n_D^{25}$: 1.5446.
(210) 2-[2-Chloro-4-(3,4-dichlorobenzyl)phenoxy]ethylamine. $n_D^{24.8}$: 1.5921.
(211) 2-[2-Chloro-4-(3,5-difluorobenzyl)phenoxy]ethylamine. $n_D^{24.8}$: 1.5761.
(212) 2-[2,5-Dichloro-4-(3,5-difluorophenoxy)phenoxy]ethylamine. $n_D^{23}$: 1.5644.
(213) 2-[2,6-Dichloro-4-(3,5-difluorophenoxy)phenoxy]ethylamine. $n_D^{23}$: 1.5737.
(214) 2-[2-Chloro-4-(3-bromophenoxy)phenoxy]ethylamine.
(215) 2-[2-Chloro-5-(3,4-dichlorophenoxy)phenoxy]ethylamine. $n_D^{23}$: 1.5624.
(216) 2-[2-Chloro-5-(3,5-difluorophenoxy)phenoxy]ethylamine. $n_D^{23}$: 1.5884.
(217) 2-[2-Chloro-4-(4-fluorophenoxy)phenoxy]ethylamine. $n_D^{25}$: 1.5721.
(218) 2-[2-Chloro-4-(4-chlorophenoxy)phenoxy]ethylamine. $n_D^{25}$: 1.5693.
(219) 2-[2-Chloro-4-(4-trifluoromethylphenoxy)phenoxy]ethylamine.

(220) 2-(2-Chloro-5-phenoxyphenoxy)ethylamine. $n_D^{24.3}$: 1.5903.

In formulation examples as hereinafter given, part(s) and % are all by weight.

FORMULATION EXAMPLE 1 (EMULSIFIABLE CONCENTRATE)

To a mixture of 10 parts of each of Compounds (1) through (154), 35 parts of xylene and 35 parts of dimethylformamide, 14 parts of polyoxyethylene styrylphenyl ether and 6 parts of calcium dodecylbenzenesulfonate are added, and the resultant mixture is thoroughly mixed while stirring to give a 10% emulsifiable concentrate.

FORMULATION EXAMPLE 2 (WETTABLE POWDER)

20 Parts of each of Compounds (1) through (154) are added to a mixture of 4 parts of sodium laurylsulfate, 2 parts of calcium ligninsulfonate, 20 parts of synthetic hydrated silica fine powders and 54 parts of diatomaceous earth, and the resultant mixture is stirred in a mixer to give a 20% wettable powder.

FORMULATION EXAMPLE 3 (GRANULES)

5 Parts of sodium dodecylbenzenesulfonate, 30 parts of bentonite and 60 parts of clay are added to 5 parts of each of Compounds (1) to (34), (36) to (47), (49) to (56), (58) to (61), (63) to (84), (86) to (99), (101) to (105), (107) to (115), (117) to (129), (131) to (142), (144) to (146), (148) to (152) and (154), and the mixture is pulverized with addition of a suitable amount of water. The mixture is granulated in a granulator and air-dried to give 5% granules.

FORMULATION EXAMPLE 4 (GRANULES)

5 Parts of synthetic hydrated silica fine powders, 5 parts of sodium dodecylbenzenesulfonate, 30 parts of bentonite and 55 parts of clay are added to 5 parts of each of Compounds (35), (48), (57), (62), (130) and (143), and the mixture is pulverized with addition of a suitable amount of water. The mixture is granulated in a granulator and air-dried to give 5% granules.

FORMULATION EXAMPLE 5 (DUSTS)

0.3 Part of each of Compounds (1) to (34), (36) to (47), (49) to (56), (58) to (61), (63) to (84), (86) to (99), (101) to (105), (107) to (115), (117) to (129), (131) to (142), (144) to (146), (148) to (152) and (154) is added to a mixture of 1 part of synthetic hydrated silica fine powders, 1 part of an aggregating agent ( "Driless B" manufactured by Sankyo Co., Ltd.) and 7.7 parts of clay, and the mixture is well pestled in a mortar and further stirred in a mixer. To the thus obtained mixture, 90 parts of cut clay are added to give dusts containing 0.3% of the active ingredient.

FORMULATION EXAMPLE 6 (DUSTS)

0.3 Part of each of Compounds (35), (48), (57), (62), (130) and (143) and 0.03 part of synthetic hydrated silica fine powders are stirred in a mixer and pulverized by a centrifugal pulverizer. 0.97 Part of synthetic hydrated silica fine powders , 1 part of "Driless B" and 7.7 parts of clay are added thereto. The resultant mixture is pestled in a mortar and stirred in a mixer. Ninety parts of cut clay are added thereto, and the resultant mixture is further mixed in a sack to give dusts containing 0.3% of the active ingredient.

FORMULATION EXAMPLE 7 (DUSTS)

0.3 Part of each of Compounds (1) to (34), (36) to (47), (49) to (56), (58) to (61), (63) to (84), (86) to (99), (101) to (105), (107) to (115), (117) to (129), (131) to (142), (144) to (146), (148) to (152) and (154), 2 parts of fenitrothion (O,O-dimethyl O-(3-methyl-4-nitrophenyl)phosphorothioate), 3 parts of synthetic hydrated silica fine powders, 1 part of "Driless B" and 77 parts of clay are pestled in a mortar and stirred in a mixer, followed by mixing in a sack to give dusts.

FORMULATION EXAMPLE 8 (DUSTS)

0.3 Part of each of Compounds (35), (48), (57), (62), (130) and (143) and 0.03 part of synthetic hydrated silica fine powders are stirred in a mixer and pulverized by a centrifugal pulverizer, followed by addition of 2 parts of fenitrothion, 2.97 parts of synthetic hydrated silica fine powders, 1 part of "Driless B" and 3.7 parts of clay. The resultant mixture is pestled in a mortar and stirred in a mixer. 90 Parts of cut clay are added thereto, and the resultant mixture is further mixed in a sack to give dusts.

FORMULATION EXAMPLE 9 (DUSTS)

0.3 Part of each of Compounds (1) to (34), (36) to (47), (49) to (56), (58) to (61), (63) to (84), (86) to (99), (101) to (105), (107) to (115), (117) to (129), (131) to (142), (144) to (146), (148) to (152) and (154) is added to a mixture of 2 parts of BPMC (O-sec-butylphenyl N-methylcarbamate), 3 parts of synthetic hydrated silica fine powders, 1 part of "Driless B" and 3.7 parts of clay, and the resultant mixture is pestled in a mortar and stirred in a mixer. 90 Parts of cut clay are added thereto, and the resultant mixture is further mixed in a sack to give dusts.

FORMULATION EXAMPLE 10 (DUSTS)

0.3 Part of each of Compounds (35), (48), (57), (62), (130) and (143) and 0.03 part of synthetic hydrated silica fine powders are stirred in a mixer and pulverized by a centrifugal pulverizer, followed by addition of 2 parts of BPMC, 2.97 parts of synthetic hydrated silica fine powders, 1 part of "Driless B" and 3.7 parts of clay. The resultant mixture is pestled in a mortar and stirred in a mixer. 90 Parts of cut clay are added thereto, and the resultant mixture is further mixed in a sack to give dusts.

FORMULATION EXAMPLE 11 (DUSTS)

To a solution of 1 part of each of Compounds (1) through (154) in an appropriate amount of acetone, 5 parts of synthetic hydrated silicon dioxide fine powders, 0.3 part of PAP (acidic isopropyl phosphate) and 93.7 parts of clay are added, and the mixture is stirred in a juice mixer, followed by evaporation of acetone to give 1% dusts.

FORMULATION EXAMPLE 12 (FLOWABLE CONCENTRATE)

10 Parts of each of Compounds (1) to (34), (36) to (47), (49) to (56), (58) to (61), (63) to (84), (86) to (99), (101) to (105), (107) to (115), (117) to (129), (131) to (142), (144) to (146), (148) to (152) and (154) are added to 40 parts of an aqueous solution containing 6 parts of polyvinyl alcohol, and the mixture is stirred in a mixer. To the resultant dispersion, 40 parts of an aqueous solution containing 0.05 part of xanthane gum and 0.1 part of aluminum magnesium silicate are added, followed by addition of 10 parts of propylene glycol. The mixture is gently stirred to give 10% flowable concentrate.

FORMULATION EXAMPLE 13 (FLOWABLE CONCENTRATE)

20 Parts of each of Compounds (35), (48), (57), (62), (130) and (143) and 1.5 parts of sorbitan trioleate are added to 28.5 parts of an aqueous solution containing 2 parts of polyvinyl alcohol, and the mixture is finely pulverized (less than 3 microns in particle size) by the aid of a sand grinder. To the resultant mixture, 40 parts of an aqueous solution containing 0.05 part of xanthane gum and 0.1 part of aluminum magnesium silicate are added, followed by addition of 10 parts of propylene glycol. The mixture is gently stirred to give 20% flowable concentrate.

FORMULATION EXAMPLE 14 (OIL SPRAY)

0.1 Part of each of Compounds (1) through (154) is dissolved in 5 parts of xylene and 5 parts of trichloroethane, and the resultant solution is mixed with 89.9 parts of deodorized kerosene to give 0.1% oil spray.

FORMULATION EXAMPLE 15 (OIL-BASED AEROSOL)

A solution of 0.1 part of each of Compounds (1) through (154), 0.2 part of tetramethrin (2,2-dimethyl-3-(2-methyl-1-propenyl)cyclopropanecarboxylic acid (1,3,4,5,6,7-hexahydro-1,3-dioxo-2H-isoindol-2-yl)methyl ester), 0.1 part of d-phenothrin (2,2-dimethyl-3-(2-methyl-1-propenyl)cyclopropanecarboxylic acid (3-phenoxyphenyl)methyl ester) in 10 parts of trichloroethane and 59.6 parts of deodorized kerosene is filled in an aerosol container. After provision of a valve, 30 parts of a propellant (liquefied petroleum gas) is filled through the valve under compression to give an oil-based aerosol.

FORMULATION EXAMPLE 16 (WATER-BASED AEROSOL)

A solution of 0.2 part of each of Compounds (1) through (154), 0.2 part of d-allethrin (2,2-dimethyl-3-(2-methyl-1-propenyl)cyclopropanecarboxylic acid 2-methyl-4-oxo-3-(2-propenyl)-2-cyclopenten-1-yl ester), 0.2 part of d-phenothrin, 5 parts of xylene, 3.4 parts of deodorized kerosene and 1 part of an emulsifier ("ATMOS 300" ® manufactured by Atlas Chemical Co., Ltd.) in 50 parts of distilled water is filled in an aerosol container. After provision of a valve, 40 parts of a propellant (liquefied petroleum gas) is filled through the valve under compression to give a water-based aerosol.

FORMULATION EXAMPLE 17 (FUMIGANT)

100 mg of each of Compounds (1) through (154) is dissolved in an appropriate amount of acetone, and the resultant solution is impregnated with a porous ceramic plate (4.0×4.0×1.2 cm) to give a fumigant.

The following test examples are given to show the biological activity of the carbamic acid derivatives (I). For comparison, a conventional insecticide as shown in Table 7 was used.

TABLE 7

| Compound symbol | Chemical structure | Remarks |
|---|---|---|
| A | ⌬—O—⌬—OCH$_2$CH$_2$NHCOC$_2$H$_5$ (C=O) | Fenoxycarb (compound described in U.S. Pat. No. 4,215,139) |

TEST EXAMPLE 1

Metamorphosis Inhibitory Activity Against Brown Rice Planthopper Nymphae

An emulfiable concentrate prepared according to Formulation Example 1 was diluted with water to make a predetermined concentration. The dilution was sprayed onto rice plants cultivated in polyethylene cups at a rate of 20 ml/2 pots on a turning table. After air-drying, the plants were infested with about ten 3rd instar nymphae of brown rice planthopper (*Nilaparvata lugens*). After 10 days, the number of normal adults was counted to obtain an emergence inhibitory rate. The results are shown in Table 8.

TABLE 8

| Compound No. | Concentration (ppm) | Inhibitory rate (%) |
|---|---|---|
| 1 | 5 | 100 |
| 2 | 5 | 100 |
| 3 | 5 | 100 |
| 5 | 5 | 100 |
| 6 | 5 | 100 |
| 7 | 5 | 100 |
| 8 | 5 | 100 |
| 9 | 5 | 100 |
| 10 | 5 | 100 |
| 11 | 5 | 100 |
|  | 0.05 | 100 |
| 12 | 5 | 100 |
| 13 | 5 | 100 |
| 14 | 5 | 100 |
| 15 | 5 | 100 |
| 16 | 5 | 100 |
|  | 0.05 | 100 |
| 17 | 5 | 100 |
| 18 | 5 | 100 |
| 20 | 5 | 100 |
| 21 | 5 | 100 |
|  | 0.05 | 100 |
| 22 | 5 | 100 |
|  | 0.05 | 100 |
| 23 | 5 | 100 |
| 24 | 5 | 100 |
| 25 | 5 | 100 |
|  | 0.05 | 100 |
| 26 | 5 | 100 |
|  | 0.05 | 100 |
| 28 | 5 | 100 |
|  | 0.05 | 100 |
| 29 | 5 | 100 |
| 30 | 5 | 100 |
| 32 | 5 | 100 |
| 39 | 5 | 100 |
| 42 | 5 | 100 |
| 51 | 5 | 100 |
| 106 | 5 | 100 |
| 124 | 5 | 100 |
|  | 0.05 | 100 |
| 125 | 5 | 100 |
|  | 0.05 | 100 |
| 127 | 5 | 100 |
|  | 0.05 | 100 |
| 134 | 5 | 100 |
| 136 | 5 | 100 |
|  | 0.05 | 100 |

TABLE 8-continued

| Compound No. | Concentration (ppm) | Inhibitory rate (%) |
|---|---|---|
| 145 | 5 | 100 |
|  | 0.05 | 100 |
| 147 | 5 | 100 |
| 154 | 5 | 100 |
|  | 0.05 | 100 |
| AA | 5 | 58 |

Compound Nos. (11), (16), (22), (25), (26), (127), (145) and (154) also showed a 100% emergence inhibitory rate at a concentration of 5 ppb.

TEST EXAMPLE 2

Reproduction Inhibitory Activity Against Green Rice Leafhopper

An emulfiable concentrate prepared according to Formulation Example 1 was diluted with water to make a predetermined concentration. The dilution was sprayed onto rice plants (about 20 cm in height) cultivated in plastic pots (1/5000 are in width) at a rate of 40 ml/2 pots on a turning table. After air-drying, the pots were covered with wire cages, and each 10 female and male adults of green rice leafhopper (*Nephotettix cincticeps*) were released in each of the cages. After 3 weeks, the number of nymphae was counted to obtain a reproduction inhibitory rate. The results are shown in Table 9.

TABLE 9

| Compound No. | Concentration (ppm) | Inhibitory rate (%) |
|---|---|---|
| 11 | 100 | 100 |
| 25 | 100 | 99 |
| 127 | 100 | 100 |
| A | 100 | 65 |

TEST EXAMPLE 3

Ovicidal Activity Against Brown Rice Planthopper

An emulfiable concentrate prepared according to Formulation Example 1 was diluted with water to make a predetermined concentration. Each 5 male and female adults of brown rice planthopper (*Nilaparvata lugens*) were released in rice plants cultivated in pots covered with a cage for 3 days in order to lay eggs. After the adults were removed, the dilution was sprayed onto the rice plants with eggs at a rate of 20 ml/2 pots on a turning table. After 14 days, the number of hatching was counted to obtain an ovicidal rate. The results are shonw in Table 10.

TABLE 10

| Compound No. | Concentration (ppm) | Ovicidal rate (%) |
|---|---|---|
| 11 | 20 | 100 |
| 16 | 20 | 100 |
| 25 | 20 | 100 |
| 127 | 20 | 100 |
| 145 | 20 | 100 |
| 154 | 20 | 100 |
| A | 20 | 20 |

What is claimed is:
1. A carbamic acid derivative of the formula:

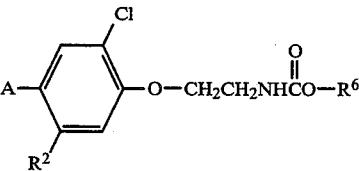

wherein A is 3,5-difluorophenoxy, 3,4-dichlorophenoxy, 3-chlorophenoxy, 4-chlorophenoxy or 4-fluorophenoxy; $R^2$ is a hydrogen atom or a chlorine atom, and $R^6$ is a methyl group, an ethyl group or a 2-chloroethyl group.

2. The carbamic acid drivative according to claim 1, wherein A is 3,5-difluorophenoxy, 3,4-dichlorophenoxy or 3-chlorophenoxy.

3. The carbamic acid derivative according to claim 1, which is ethyl 2-(2-chloro-4-(3,5-difluorophenoxy)-phenoxy)ethylcarbamate.

4. The carbamic acid derivative according to claim 1, which is ethyl 2-[2,5-dichloro-4-(3,5-difluorophenoxy)-phenoxy]ethylcarbamate.

5. The carbamic acid derivative according to claim 1, which is ethyl 2-[2-chloro-4-(3,4-dichlorophenoxy)-phenoxy]ethylcarbamate.

6. The carbamic acid derivative according to claim 1, which is 2-chloroethyl 2-[2-chloro-4-(3,5-difluorophenoxy)phenoxy]ethylcarbamate.

7. The carbamic acid derivative according to claim 1, which is ethyl 2-[2-chloro-4-(4-fluorophenoxy)phenoxy]ethylcarbamate.

8. The carbamic acid derivative according to claim 1, which is ethyl 2-[2-chloro-4-(4-chlorophenoxy)phenoxy]ethylcarbamate.

9. The carbamic acid derivative according to claim 1, which is ethyl 2-[2-chloro-4-(3-chlorophenoxy)phenoxy]ethylcarbamate.

10. The carbamic acid derivative according to claim 1, which is methyl 2-[2-chloro-4-(3,5-difluorophenoxy)-phenoxy]ethylcarbamate.

11. The carbamic acid derivative according to claim 1, which is methyl 2-[2-chloro-4-(3-chlorophenoxy)-phenoxy]ethylcarbamate.

12. The carbamic acid derivative according to claim 1, which is ethyl 2-[2,5-dichloro-4-(3-chlorophenoxy)-phenoxy]ethylcarbamate.

13. The carbamic acid derivative according to claim 1, which is methyl 2-[2-chloro-4-dichlorophenoxy)-phenoxy]ethylcarbamate.

14. The carbamic acid derivative according to claim 1, which is isopropyl 2-[2-chloro-4-(3,5-difluorophenoxy)phenoxy]ethylcarbamate.

15. The carbamic acid derivative according to claim 1, wherein A is 3,5-difluorophenoxy or 3-chlorophenoxy, $R^2$ is a hydrogen atom, and $R^6$ is a methyl group or a 2-chloroethyl group.

16. A composition for controlling insect pests which comprises an effective amount of the carbamic acid derivative according to claim 1 as an active ingredient and an inert carrier.

17. A method for controlling insect pests which comprises applying an effective amount of the carbamic acid derivative according to claim 1 to the insect pests or the locus where the insect pests propogate.

* * * * *